United States Patent
Welzel et al.

(10) Patent No.: US 10,086,123 B2
(45) Date of Patent: *Oct. 2, 2018

(54) INTEGRATED DEVICE FOR LIVER SUPPORT SYSTEM

(71) Applicant: GAMBRO LUNDIA AB, Lund (SE)

(72) Inventors: Arne Welzel, Hechingen (DE); Markus Storr, Filderstadt (DE); Bernd Krause, Rangendingen (DE); Hermann Goehl, Bisingen-Zimmern (DE); Ralf Flieg, Rangendingen (DE)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/646,833

(22) PCT Filed: Nov. 5, 2013

(86) PCT No.: PCT/EP2013/073045
§ 371 (c)(1),
(2) Date: May 22, 2015

(87) PCT Pub. No.: WO2014/079679
PCT Pub. Date: May 30, 2014

(65) Prior Publication Data
US 2015/0290380 A1    Oct. 15, 2015

(30) Foreign Application Priority Data

Nov. 26, 2012    (EP) .................................... 12194165

(51) Int. Cl.
*A61M 1/16*    (2006.01)
*B01J 20/28*    (2006.01)
(Continued)

(52) U.S. Cl.
CPC ............ *A61M 1/1633* (2014.02); *A61M 1/16* (2013.01); *A61M 1/1621* (2014.02);
(Continued)

(58) Field of Classification Search
CPC ...... B01D 63/02; B01D 63/04; B01D 63/021; B01D 61/00; B01D 61/243; B01D 61/30;
(Continued)

(56) References Cited

U.S. PATENT DOCUMENTS

| 3,503,515 | A | 3/1970 | Tomsic |
| 4,784,768 | A | 11/1988 | Mathieu |

(Continued)

FOREIGN PATENT DOCUMENTS

| EP | 0341413 | 11/1989 |
| EP | 0 615 780 A1 | 9/1993 |

(Continued)

OTHER PUBLICATIONS

International Search Report from related WO 2014/079679 dated Feb. 4, 2014, 3 pages.

(Continued)

*Primary Examiner* — Vickie Y Kim
*Assistant Examiner* — Benjamin L Lebron
(74) *Attorney, Agent, or Firm* — Barnes & Thornburg LLP

(57) ABSTRACT

An extracorporeal system for liver dialysis comprises a filter device having hollow fibers with integrated ion-exchange particles and hydrophobic adsorbent particles in the filtrate space. The system can be used for the treatment of acute liver failure and acute-on-chronic liver failure.

18 Claims, 13 Drawing Sheets

(51) Int. Cl.

| | | |
|---|---|---|
| *A61M 1/34* | (2006.01) | |
| *B01D 69/14* | (2006.01) | |
| *B01D 15/32* | (2006.01) | |
| *B01D 15/36* | (2006.01) | |
| *B01D 63/02* | (2006.01) | |
| *B01D 15/26* | (2006.01) | |
| *B01J 47/014* | (2017.01) | |
| *A61M 1/26* | (2006.01) | |
| *B01D 71/42* | (2006.01) | |
| *B01D 71/56* | (2006.01) | |
| *B01D 71/68* | (2006.01) | |
| *B01D 63/04* | (2006.01) | |
| *B01D 61/24* | (2006.01) | |
| *B01D 61/30* | (2006.01) | |
| *B01J 20/20* | (2006.01) | |
| *B01J 20/26* | (2006.01) | |
| *B01J 20/10* | (2006.01) | |
| *B01D 15/38* | (2006.01) | |
| *B01D 69/08* | (2006.01) | |
| *D01D 5/24* | (2006.01) | |

(52) U.S. Cl.
CPC .......... *A61M 1/1696* (2013.01); *A61M 1/26* (2013.01); *A61M 1/34* (2013.01); *A61M 1/3472* (2013.01); *A61M 1/3475* (2014.02); *A61M 1/3486* (2014.02); *B01D 15/265* (2013.01); *B01D 15/322* (2013.01); *B01D 15/325* (2013.01); *B01D 15/362* (2013.01); *B01D 15/363* (2013.01); *B01D 61/243* (2013.01); *B01D 61/30* (2013.01); *B01D 63/02* (2013.01); *B01D 63/022* (2013.01); *B01D 63/023* (2013.01); *B01D 63/04* (2013.01); *B01D 69/08* (2013.01); *B01D 69/147* (2013.01); *B01D 71/42* (2013.01); *B01D 71/56* (2013.01); *B01D 71/68* (2013.01); *B01J 20/103* (2013.01); *B01J 20/20* (2013.01); *B01J 20/261* (2013.01); *B01J 20/28023* (2013.01); *B01J 20/28028* (2013.01); *B01J 47/014* (2017.01); *A61M 1/3413* (2013.01); *A61M 1/3437* (2014.02); *A61M 2205/75* (2013.01); *A61M 2210/1071* (2013.01); *B01D 15/3804* (2013.01); *B01D 63/021* (2013.01); *B01D 2311/06* (2013.01); *B01D 2311/2623* (2013.01); *B01D 2311/2626* (2013.01); *B01D 2313/40* (2013.01); *B01D 2325/12* (2013.01); *B01D 2325/20* (2013.01); *B01D 2325/36* (2013.01); *B01D 2325/38* (2013.01); *B01D 2325/42* (2013.01); *D01D 5/24* (2013.01)

(58) Field of Classification Search
CPC .... B01D 15/12; B01D 15/322; B01D 15/325; B01D 15/362; B01D 15/363; B01D 15/3804; B01D 15/265; B01D 2313/40; B01D 71/42; B01D 71/56; B01D 71/68; B01D 2311/06; B01D 2311/2623; B01D 2311/2626; B01D 2325/36; B01D 2325/38; B01D 2325/42; B01D 63/022; B01D 63/023; B01D 69/08; B01D 69/147; B01D 2325/12; B01D 2325/20; B01J 20/28014; B01J 20/103; B01J 20/20; B01J 20/261; B01J 47/003; B01J 20/28023; B01J 20/28028; B01J 47/014; C07K 1/34; A61M 1/1633; A61M 1/1621; A61M 1/1696; A61M 1/26; A61M 2205/75; A61M 2210/1071; A61M 1/16; A61M 1/34; A61M 1/3413; A61M 1/3437; A61M 1/3472; A61M 1/3475; A61M 1/3486; D01D 5/24
See application file for complete search history.

(56) References Cited

U.S. PATENT DOCUMENTS

| | | | |
|---|---|---|---|
| 6,497,675 | B1* | 12/2002 | Davankov .......... A61M 1/3472 210/433.1 |
| 6,709,598 | B1 | 3/2004 | Pearl |
| 2003/0111414 | A1 | 6/2003 | Baurmeister et al. |
| 2004/0069710 | A1 | 4/2004 | Sirkar |
| 2005/0015040 | A1 | 1/2005 | Wuepper et al. |
| 2005/0029193 | A1 | 2/2005 | Matson et al. |
| 2006/0099414 | A1* | 5/2006 | Koops .................. B01J 47/018 428/364 |
| 2008/0185322 | A1 | 8/2008 | Christmann et al. |
| 2009/0304677 | A1 | 12/2009 | Ichim et al. |
| 2010/0004588 | A1 | 1/2010 | Yeh et al. |
| 2011/0040228 | A1* | 2/2011 | Radunsky .......... A61M 1/3413 604/5.04 |
| 2011/0094962 | A1 | 4/2011 | Heinrich et al. |
| 2011/0218512 | A1 | 9/2011 | Tullis et al. |
| 2012/0226258 | A1 | 9/2012 | Otto et al. |
| 2012/0305487 | A1 | 12/2012 | Beck et al. |

FOREIGN PATENT DOCUMENTS

| | | | |
|---|---|---|---|
| EP | 1 257 333 | | 8/2001 |
| EP | 1518870 | | 3/2005 |
| EP | 1627941 | | 2/2006 |
| EP | 1 875 956 A1 | | 7/2006 |
| EP | 1 875 957 A1 | | 7/2006 |
| EP | 1685862 | | 8/2006 |
| EP | 2113298 | | 11/2009 |
| EP | 2 380 610 A1 | | 4/2010 |
| EP | 2281625 | | 2/2011 |
| EP | 2 604 331 A1 | | 12/2011 |
| EP | 2 735 360 A1 | | 11/2012 |
| GB | 1470206 | | 4/1977 |
| WO | 9108782 | | 6/1991 |
| WO | 99/25726 A1 | | 5/1999 |
| WO | 9925726 | | 5/1999 |
| WO | 0067885 | | 11/2000 |
| WO | 01/60477 A2 | | 8/2001 |
| WO | 2004/003268 A1 | | 1/2004 |
| WO | 2004014315 | | 2/2004 |
| WO | 2004056460 | | 7/2004 |
| WO | WO 2006019293 A1 * | | 2/2006 .............. D01D 5/06 |
| WO | 2012/142180 A1 | | 10/2012 |
| WO | 2012142180 | | 10/2012 |
| WO | WO 2014079680 A1 * | | 5/2014 .............. B01D 63/02 |

OTHER PUBLICATIONS

PCT International Search Report, International Application No. PCT/EP2013/073056, dated Dec. 20, 2013, 4 pages.
Aimar et al, A Contribution to the Translation of Retention Curves into Pore Size Distributions for Sieving Membranes, Journal of Membrane Science, 54, (1990), pp. 321-338.
Boldt, Use of Albumin: An Update, British Journal of Anaesthesia 104 (3): doi: 10.1093/bja/aep393, (2010), pp. 246-284.
Cardiovascular Implants and Extracorporeal Systems—Haemodialysers, Haemodiafilters, Haemofilters and Haemoconcentrators, International Standard, Reference No. ISO 8637, Third edition Jul. 1, 2010, 28 pages.
Stauber et al, MARS and Prometheus in Acute-on-Chronic Liver Failure: Toxin Elimination and Outcome, Transplantationsmedizin, (2010), 22. Jahrg., S., pp. 333-338.
Honore et al, Hemofiltration, Adsorption, Sieving and the Challenge of Sepsis Therapy Design, (2002), 4 pages, BioMed Central Ltd (Print ISSN 1364-8535; Online ISSN 1466-609X), http://ccforum.com/content/6/5/394.

(56) References Cited

OTHER PUBLICATIONS

Metallic powders —Determination of tap density (ISO 3953:2011); German version EN ISO 3953:2011, 2011, 9 pages.
PCT International Search Report, International Application No. PCT/EP2013/073045, dated Feb. 12, 2014, 3 pages.
PCT International Search Report, International Application No. PCT/EP2013/073058, dated Mar. 13, 2014, 6 pages.

* cited by examiner

INTEGRATED DEVICE FOR LIVER SUPPORT SYSTEM

CROSS REFERENCE TO RELATED APPLICATIONS

This application is the U.S. national phase of PCT/EP2013/073045 filed Nov. 5, 2013. PCT/EP2013/073045 claims benefit under the Paris Convention to EP 12194165.2 filed Nov. 26, 2012. The disclosures of both EP 12194165.2 and PCT/EP2013/073045 are hereby incorporated herein in their entireties.

TECHNICAL FIELD

The present disclosure relates to an extracorporeal system for liver dialysis, comprising a filter device having combined therein hollow fibers with integrated ion-exchange particles and hydrophobic adsorbent particles in the filtrate space. The system can be used for the treatment of acute liver failure and acute-on-chronic liver failure.

DESCRIPTION OF THE RELATED ART

Liver dialysis is a detoxification treatment for liver failure and is used for patients with various liver disorders, such as, for example, hepatorenal syndrome, decompensated chronic liver disease, acute liver failure, graft dysfunction after liver transplantation, liver failure after liver surgery, secondary liver failure, multi organ failure or intractable pruritus in cholestasis. It is similar to hemodialysis and based on the same principles. Like a bioartificial liver device, it is a form of artificial extracorporeal liver support.

The so-called hepatorenal syndrome (HRS) is a life-threatening medical condition that consists of rapid deterioration in kidney function in individuals with cirrhosis or massive liver failure. HRS is usually fatal unless a liver transplant is performed, although various treatments, such as dialysis, can prevent advancement of the condition.

HRS can affect individuals with cirrhosis (regardless of cause), severe alcoholic hepatitis, or massive hepatic failure, and usually occurs when liver function deteriorates rapidly because of an acute injury such as an infection, bleeding in the gastrointestinal tract, or overuse of diuretic medications. HRS is a relatively common complication of cirrhosis, occurring in 18% of cirrhotics within one year of their diagnosis, and in 39% of cirrhotics within five years of their diagnosis. Deteriorating liver function is believed to cause changes in the circulation that supplies the intestines, altering blood flow and blood vessel tone in the kidneys. The renal failure of HRS is a consequence of these changes in blood flow, rather than direct damage to the kidney. Two forms of hepatorenal syndrome have been defined: Type 1 HRS entails a rapidly progressive decline in kidney function, while type 2 HRS is associated with ascites (fluid accumulation in the abdomen) that does not improve with standard diuretic medications.

For example, the risk of death in hepatorenal syndrome is very high; the mortality of individuals with type 1 HRS is over 50% over the short term. The only long-term treatment option for the condition is liver transplantation. As a short-term treatment option before transplantation, liver dialysis may turn out to be vitally important for the patient.

A critical issue of the clinical syndrome in liver failure is the accumulation of toxins not cleared by the failing liver. Based on this hypothesis, the removal of lipophilic, albumin-bound substances such as bilirubin, bile acids, metabolites of aromatic amino acids, medium-chain fatty acids and cytokines should be beneficial to the clinical course of a patient in liver failure.

In liver dialysis systems, such as the Molecular Adsorbent Recycling System (MARS®), blood is cleansed in an extracorporeal circuit that is a combination of both kidney and liver dialysis (FIG. 1). Established methods for kidney dialysis alone are not applicable for liver failure because kidney dialysis removes water-soluble toxins only. The liver normally removes albumin bound toxins. Albumin is a protein found in the blood that carries water insoluble substances including toxins. For this reason, systems like the MARS® system make use of human albumin to cleanse the blood because the albumin removes the toxins which are bound to albumin in the blood that the aqueous solution in kidney dialysis cannot remove, such as unconjugated bilirubin, bile acids, hydrophobic amino and fatty acids. A significant portion of toxins are water-soluble molecules of low- and middle-molecular weight, the concentration of which may be increased by hepatic failure and renal failure. These molecules can effectively be removed by hemodialysis. The MARS® system is thus thought to replace the detoxification function of the liver with regard to water-soluble and albumin-bound toxins. The principles of this system are already described in EP 0 615 780 A1.

Another known liver support system, the Prometheus® system, (FPSA, fractionated plasma separation and adsorption) is based on fractionated plasma separation across an albumin-permeable filter (AlbuFlow®) and high-flux dialysis in the blood circuit. The system utilizes a so-called AlbuFlow® membrane, which is permeable for larger proteins such as albumin. In this system the blood is first pumped through the AlbuFlow® filter that retains blood cells and large protein molecules. The blood liquid, or plasma, along with albumin and smaller protein molecules is then fed through two adsorbers that separate toxins from the albumin and bind them. Following adsorption, the blood plasma with the detoxified albumin is joined with the blood cells retained by the AlbuFlow filter. Finally, the blood is dialyzed to remove the remaining water-soluble toxins, and the filtered blood is then reintroduced into the patient. The system does not require exogenous albumin in the secondary circuit since endogenous albumin enters the secondary circuit via the AlbuFlow® membrane. Like the MARS® system, the Prometheus® system makes use of at least two adsorber units in the secondary circuit.

As shown in FIG. 1, the patient's (1) blood in the current MARS® system is passed into a hollow fiber membrane hemodialyzer (3). The dialysate side of the dialyzer (3) provides for clean human albumin that acts as a dialysate. As the patient's blood moves along the membrane, water-soluble and protein bound toxins in the blood are transported through the membrane and into the dialysate albumin solution on the other side (8). The membrane is impermeable to albumin and to other valuable proteins such as hormones and clotting factors, keeping them in the patient's circulation. The cleansed blood then returns to the patient. Meanwhile, the albumin solution carrying the toxins is recycled by passing first through a low-flux dialyzer (4) opposite of a buffered aqueous solution. This process is similar to that found in kidney dialysis and removes water-soluble substances from the albumin solution. The albumin then passes through an activated carbon adsorber (5) and, after passing a filter which removes carbon particles (6), passes through an anion exchanger (7) that removes toxins bound to albumin. The recycled albumin can then again enter the dialyzer (3) and bind again to toxins which can thus be removed from the patient's blood. The albumin recycling described comprises four major components, which is the low-flux dialyzer (4), the carbon adsorber cartridge (5), the filter for carbon particles (6) and finally another device, the anion exchanger (7).

Both the MARS® system and the Prometheus® system, especially in the albumin circle, involve the use of at least two adsorber modules and are thus comparatively complex in handling and in parts also costly. In such systems, for example the current MARS® system, it would thus be desirable to combine certain components and the related functions within one single device for improving cost and handling aspects, and at the same time to improve the efficiency of the system especially with regard to the elimination kinetics of certain unwanted molecules, such as unconjugated bilirubin, bile acid and/or IL-6. It is known that the current systems have limitations with regard to their elimination performance concerning strongly bound toxins, such as unconjugated bilirubin. The accumulation of pro-inflammatory cytokines in acute liver failure is associated with a high mortality. IL-6, IL-1β and TNF are known to induce massive necrotic inflammation of liver tissue.

The applicants have now developed a device which is able to combine the functions of at least three of the aforementioned four components of the secondary albumin circuit. The device replaces first the carbon adsorber cartridge (5), the carbon particle filter (6) and finally the anion exchange module (7) and integrates all functions into one module by incorporating finely dispersed ion exchange particles into a hollow fiber membrane, which is used to prepare a hollow fiber bundle which is transferred into a cylindrical filter housing. The filtrate space of said housing is filled with a hydrophobic adsorber resin, which incorporates the function for example of a carbon adsorber cartridge into the new device. The use of a membrane further avoids the need to use any particle filter such as the carbon particle filter (6) in the MARS® system, as the membrane is designed to avoid the passage of any particles of the hydrophobic adsorber resin through the hollow fiber membrane wall. Said module can replace the above-mentioned standard components which are currently used in the MARS® system and improve the cost and handling efficiency of the complete system. At the same time, the new device is able to significantly improve the detoxification efficiency of the system. In particular, strongly albumin bound liver toxins, such as unconjugated bilirubin, bile acid and inflammatory cytokines such as interleukin 6 (IL-6) are removed with increased efficiency. Moreover, the pressure drop in the integrated device contemplated here could be shown to be lower compared to the adsorber units which are currently in use in liver support systems.

Such device can be used in all liver support systems which are designed to remove liver toxins, including albumin bound liver toxins, from the dialysate of a first blood circuit, wherein the dialysate comprises either endogenous or exogenous albumin and toxins bound thereto, and wherein the albumin is recovered by capturing the toxins in the dialysate in a secondary circuit before the recovered albumin is re-introduced into the blood circuit.

The invention thus provides an improved integrated device for the removal of albumin bound liver toxins from a fluid for use in extracorporeal liver support systems for the treatment of liver failure.

Membranes which have incorporated therein certain particulate material have been described before in the art. For example, WO 2004/003268 A1 describes a basic approach for the preparation of porous polymeric fibers comprising a broad variety of functionalizes or active particles, comprising also ion exchange particles. EP 11193795.9 further describes how hollow fiber membranes with smaller wall size can be prepared by incorporating finely grinded material. Both references are mostly concerned with methods of producing such membranes and do not describe any specific devices which make use of the doped membranes in certain applications such as liver dialysis.

Hollow fiber filter modules which comprise particulate material on the filtrate side are also generally known in the art. Examples for devices which make use of this principle are described, for example, in US 2011/0218512 A1, which relates to antiviral therapy methods comprising passing blood or plasma through a lectin affinity hemodialysis device. In the device, blood is passed through the lumen of a hollow fiber membrane, wherein lectins are located in the extraluminal space of the cartridge, which accepts and immobilizes the viruses. US 2009/0304677 A1 relates to methods for removing microvesicular particles such as exosomes from blood, wherein, in one specific embodiment, the blood is run through an extracorporeal circulation circuit that uses a hollow fiber cartridge. However, no filter devices have become known so far which combine hollow fiber membranes having incorporated therein functional particles on the one hand, and active, particulate material on the filtrate side of the membrane on the other hand, thus combining, in one device, several functionalities which otherwise have to me served with several devices. The present invention describes such devices for the first time and also describes their use in liver support systems.

SUMMARY

It is an object of the present invention to provide an improved integrated device for the removal of albumin bound liver toxins from a fluid for use in extracorporeal liver support systems for the treatment of liver failure. The integrated device for the capture of bound liver toxins from a fluid comprises at least a bundle of hollow fiber membranes which have incorporated therein ion exchange material and further comprises at least one hydrophobic adsorber material which is located in the filtrate space of the module.

It is another object of the present invention to provide an integrated filter module (12) for the treatment of fluids, comprising a cylindrical filter housing (13); a bundle of essentially parallel hollow fiber membranes (14) distributed longitudinally within the housing (13); a filtrate space (15), which is closed off from the lumen space of the hollow fiber membranes (14) and which is in fluid communication with an inlet means (18) and optionally an outlet means (20); an inlet means (18) for feeding the fluid into the filtrate space (15) or an inlet means (21) for feeding the fluid into the lumen space of the hollow fiber membranes (14); an outlet means (19) for removing the treated fluid from the lumen of the hollow fiber membranes (3), and optionally a second outlet means (20) for removing treated fluid from the filtrate space (15), characterized in that the hollow fiber membranes (14) are prepared from at least one hydrophobic polymer selected from the group consisting of polysulfones, polyethersulfones, polyaryethersulfones, polyamides and polyacrylonitriles and at least one hydrophilic polymer and have incorporated therein 1-40 wt.-% of ion exchange particles and/or hydrophobic particles, and in that the filtrate space (15) is populated with hydrophobic and/or ion exchange particles (22).

It is another object of the present invention to provide an integrated filter module (12) for the treatment of fluids, wherein the hydrophobic particles which populate the filtrate space (15) of the module are selected from the group consisting of carbonaceous adsorbents, polymer adsorbents and hydrophobic silica or mixtures thereof.

It is another object of the present invention to provide an integrated filter module (12) for the treatment of fluids, wherein the hollow fiber membrane (14) which is used in the device comprises 1-40 wt.-% of anion exchange particles and that the filtrate space (15) is populated with hydrophobic particles.

It is another object of the present invention to provide a liver dialysis device for conducting hemodialysis on a patient suffering from liver failure, characterized in that the device comprises an integrated filter module (12), wherein the module (12) comprises a bundle of hollow fiber membranes (14) comprising 1-40 wt.-% of anion exchange particles and wherein the filtrate space (15) of the module (12) is populated with hydrophobic particles.

It is another object of the present invention to provide an integrated filter module (12) for the removal of liver toxins from fluids in extracorporeal therapies and for use in liver support systems.

It is also an object of the present invention to provide for a hollow fiber membrane module (12), wherein the module (12) comprises a bundle of hollow fiber membranes (14) comprising 1-40 wt.-% of ion exchange particles and wherein the filtrate space (15) of the module (12) is populated with hydrophobic particles for affinity chromatography.

BRIEF DESCRIPTION OF THE DRAWINGS

In FIG. 1A the dialysate side of the dialyzer provides for a dialysate solution comprising clean human albumin (8). Water-soluble and protein bound toxins in the blood are transported through the membrane of dialyzer (3) and into the dialysate albumin solution on the other side. The cleansed blood returns to the patient. This part of the system can be referred to as the "blood circuit" (9). In FIG. 1A, the albumin solution carrying the toxins is recycled by passing first through a low-flux dialyzer (4) opposite of a buffered aqueous solution, wherein water-soluble toxins can be removed by means of normal hemodialysis. The albumin then passes through an activated carbon adsorber (5) and, after passing a filter which removes carbon particles (6), passes through an anion exchanger (7). This part of the system may be referred to as the "albumin circuit" or "dialysate circuit" (10), wherein toxins, comprising also protein-bound toxins, are removed. The recycled albumin can then again enter the dialyzer (3). In FIG. 1B the albumin carrying solution passes two adsorber units (5) and (7) before the fluid again enters the blood circuit (9). The dialysis machine used within the system is displayed as (2). Circles (○) denote pumps.

FIGS. 4B and C show details of the doped hollow fiber membranes (14) which are used in such device. In FIG. 4C the material which is integrated into the membrane wall can be seen. FIG. 4D finally shows details of the active particulate material (21) which populates the filtrate space of the device. FIG. 4A again shows the entry site (outlet means (18)) of the fluid to be treated and the general flow path of the fluid through the device. Arrows symbolize that the fluid after having contacted the particulate material passes the hollow fiber membrane wall and leaves the device through the lumen of the hollow fibers and finally through outlet means (19).

FIG. 8 shows the results for unconjugated bilirubin, FIG. 9 for chenodeoxycholic acid, FIG. 10 for diazepam and FIG. 11 for interleukin-6.

FIG. 14 shows the reduction of UCB. The adsorption kinetics is better for the integrated filter module compared to the conventional cartridge system. The alternative setup with a doped membrane filter and separate cartridge with hydrophobic adsorber performs essentially as good as the integrated system. FIG. 15 shows the results for CDCA reduction. The integrated filter module and the alternative concept with a doped membrane filter and separate cartridge with hydrophobic adsorber perform better than the conventional system with two cartridges. FIG. 16 shows the reduction of diazepam. After about 2 h the quantification limit was already reached with the integrated filter module and the alternative design with a doped membrane filter and separate cartridge, whereas the conventional cartridge system reached the quantification limit only after 9 h.

DETAILED DESCRIPTION

Figure 1:
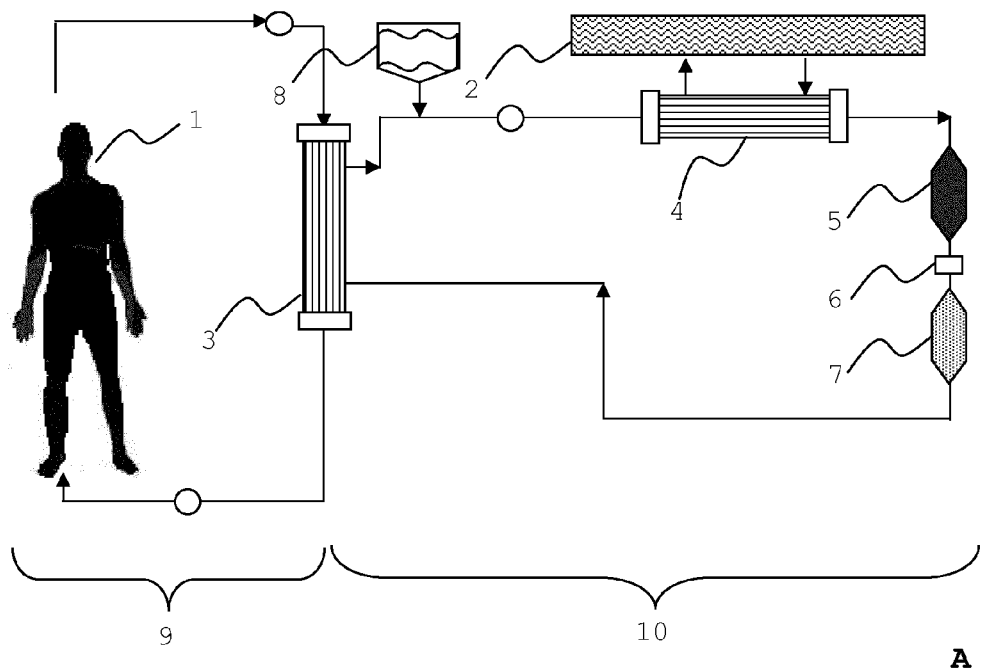
FIG. 1 shows the schematic setup of the MARS® liver support system (FIG. 1A) and the schematic setup of the Prometheus® system (FIG. 1B), wherein adsorbent units are used for removing bound liver toxins from a fluid in a secondary circuit. The patient's (1) blood is passed into a hollow fiber membrane dialyzer (3).
Figure 1:
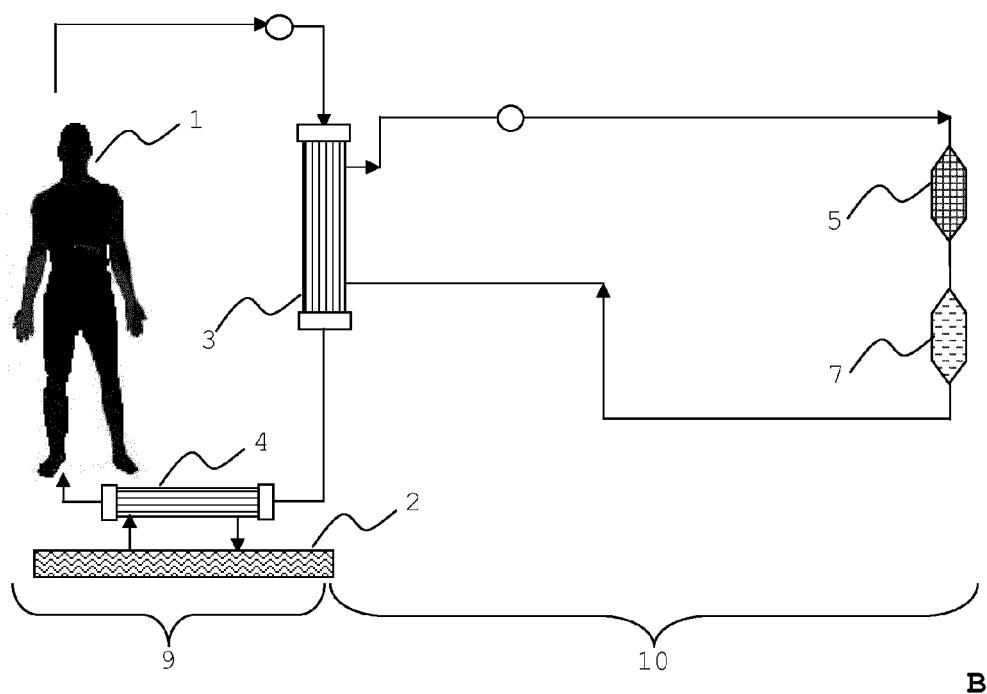

According to one aspect of the present invention, an improved integrated device is provided for the removal of albumin bound liver toxins from a fluid and for use in extracorporeal liver support systems for the treatment of liver failure. The integrated device is designed to be used for affinity chromatography, especially for being able to capture bound liver toxins from a fluid. The integrated device comprises at least a bundle of hollow fiber membranes which have incorporated therein ion exchange material and further comprises at least one hydrophobic adsorber material which is located in the filtrate space of the module. In the context of the present invention, the expression "adsorption" refers to the preferential partitioning of substances from liquid phase onto the surface of a solid substrate (the particulate material). Physical adsorption is caused mainly by van der Waals forces and electrostatic forces between adsorbate molecules and the atoms which compose the adsorbent surface. Thus adsorbents are characterized mainly by surface properties such as surface area and polarity.

According to one embodiment of the invention, the integrated filter module (12) for the treatment of fluids comprises a cylindrical filter housing (13) wherein a bundle of essentially parallel hollow fiber membranes (14) are distributed longitudinally within the housing (13). The housing (13) further comprises a filtrate space (15), which is closed off from the lumen space of the hollow fiber membranes (14) and which is in fluid communication with an inlet means (18) and optionally an outlet means (20). Inlet means (18) serves for feeding the fluid to be treated into the filtrate space (15). Alternatively, inlet means (21) serves for feeding the fluid into the lumen space of the hollow fiber membranes (14). An outlet means (19) is use for removing the treated fluid from the lumen of the hollow fiber membranes (3), and optionally a second outlet means (20) is used in for additionally removing treated fluid from the filtrate space (15). The integrated filter module (12) is characterized in that the hollow fiber membranes (14) are prepared from at least one hydrophobic polymer selected from the group consisting of polysulfones, polyethersulfones, polyaryethersulfones, polyamides and polyacrylonitriles and at least one hydrophilic polymer and have incorporated therein 1-40 wt.-%, preferably 5-40 wt.-% of ion exchange particles and/or hydrophobic particles, and in that the filtrate space (15) is populated with hydrophobic and/or ion exchange particles (22).

Such integrated filter module can be used for affinity chromatography. The filter module is especially useful for removing liver toxins from a fluid which is generated in the course of liver dialysis. The fluid may be the dialysate which is generated by a hemodialyzer during the treatment, wherein the dialysate is enriched with exogenous albumin which serves for binding liver toxins which have passed the hemodialyzer membrane wall. The liver toxins can be cleared from the dialysate by passing the dialysate through the integrated filter module of the present invention and the recycled dialysate comprising the albumin can be used again in the system. The fluid may also consist of the permeate (e.g. the plasma) of a hemodialyzer which comprises albumin having bound thereto the liver toxins which have to be cleared from the system. Such fluid or plasma can also be fed through the integrated device of the present invention and liver toxins can be removed therefrom.

According to one aspect of the present invention, the hollow fiber membranes which are used within the integrated filter module have incorporated therein 5-40 wt.-% of ion exchange particles and/or hydrophobic particles relative to the total weight of the membrane. The expression "particles" as used herein, refers to solid or gel-like fragments of certain solid or gel-type materials, such as ion exchange materials. The expression "ion exchange material" as used herein, refers to an insoluble polymeric matrix containing labile ions capable of exchanging with ions in the surrounding medium. The preparation of such hollow fiber membranes, also referred to as "doped membranes", is described in detail in EP 11193795.9.

In a specific aspect of the present invention, the particle load in said doped membranes should be in the range of between 5 wt.-% and 40 wt.-% relative to the total weight of the membrane. In yet another aspect of the present invention, the particle load should be in a range of from 20 wt.-% and 35 wt.-% of the total weight of the membrane.

In another specific aspect of the invention, the entrapped particles have an average diameter of below 20 µm, preferably below 15 µm, and especially below 10 µm. According to one aspect of the present invention, the average diameter of the entrapped particles should be below 15 µm. According to another aspect of the present invention, the average diameter of the entrapped particles should be in a range of from 0.1 µm to 10 µm.

According to one embodiment of the invention, hollow fiber membranes with basic anion exchange particles are used in modules according to the invention. Such anion exchange particles may be based, for example, on polystyrene or styrene-divinylbenzene polymers which may be unmodified or modified with sulphonic acids, polyamines or quaternary or tertiary amines. According to one aspect of the invention, the particles are based on a copolymer of styrene and divinylbenzene carrying active groups such as quaternary ammonium groups, dimethylethanolamine groups, dimethylethanolbenzyl ammonium groups, benzyltrialkyl ammonium groups, benzyldimethyl(2-hydroxyethyl) ammonium and/or trimethylbenzyl ammonium functional groups. According to a specific aspect of the present invention, the particles used are based on a copolymer of styrene and divinylbenzene carrying quaternary ammonium groups. According to another aspect of the invention, the copolymer of styrene and divinylbenzene carries trimethylbenzylammonium functional groups and is known as Cholestyramine, Cuemid, MK-135, Cholbar, Cholbar, Questran, Quantalan, Colestyramine or Dowex® 1×2-Cl. According to one embodiment of the invention, anion exchange particles which are used which are known under the trade name Dowex® 1×2, 1×4 or 1×8, each with different mesh sizes. This Dowex® series, for example Dowex® 1×2, is again based on a microporous copolymer of styrene and divinylbenzene (DVB). The functional group here is trimethylbenzylammonium group. Dowex® 1×2 (chloride form) is exemplarily shown in Formula (I) below.

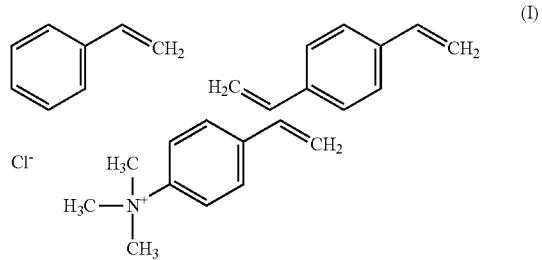

(I)

Anion exchange particles which may also be used in the hollow fiber membranes of the modules according to the invention are known, for example, under the trade name Amberlite®. Amberlite® comprises, for example, a matrix formed of styrene-divinylbenzene having active or functional groups such as quaternary ammonium groups, bezyldimethyl (2-hydroxyethyl) ammonium groups or dimethylethanolamine groups. In yet another aspect of the present invention, the particles entrapped in the hollow fiber membranes of the module of the invention are based on vinylimidazolium methochloride vinylpyrrolidone copolymers, known, for example, as Luviquat®.

Cation exchange particles which may be used in hollow fiber membranes of modules according to the invention are generally based on matrices of agarose, cellulose, dextran, methacrylate, polystyrene or polyacrylic acid. They are generally known and commercially available, for example, under trade names such as Sepharose® CM, CM, Sephadex, Toyopearl®, Amberlite®, Diaion™, Purolite®, Dowex® and Duolite® SO$_3$H, respectively.

According to another aspect of the present invention, the particles entrapped in the hollow fiber membranes of a module according to the invention are uncharged, hydrophobic particles, comprising carbonaceous adsorbents, polymer adsorbents and hydrophobic silica or combinations thereof. Examples which can be mentioned are, for example, styrenic polymers like DOWEX™ OPTIPORE™ L493 and V493 or Amberlite® XAD®-2, polydivinylbenzene polymers or styrene-divinylbenzene copolymers (e.g. Amberlite® XAD4), poly(1-phenylethene-1,2-diyl) (Thermocole), activated carbon, carbon nanotubes, or hydrophobic silica, which is silica that has hydrophobic groups chemically bonded to the surface, or combinations thereof. Hydrophobic silica can be made both from fumed and precipitated silica. Carbon particles which may be used in hollow fibers of modules according to the invention can be derived, for example, from carbon such as Printex® XE2 (Degussa AG). Such particles may be present within the hollow fiber membrane alone or in combination with the anion or cation exchange particles described above.

The hollow fiber membranes which can be used in a module according to the invention can be prepared by grinding the respective particles to an average diameter of about 20 µm or less in an aqueous solution, optionally in the presence of PVP and/or an organic solvent. The grinded particles can then optionally be suspended in an organic solvent. At least one hydrophilic and at least one hydrophobic polymer are combined with the suspension and the polymer particle suspension is stirred in order to obtain a homogeneous polymer solution wherein the particles are suspended. The polymer particle suspension is then degassed and the polymer particle suspension is extruded through an outer ring slit of a nozzle, wherein a center fluid is extruded through an inner opening of the nozzle and wherein the polymer solution on the outside of the precipitating fiber is optionally exposed to a humid steam/air mixture comprising a solvent in a content of between 0 and 10% by weight related to the water content. The precipitating fiber is immersed in a bath of non-solvent an washed and optionally dried and sterilized.

According to a further aspect of the present invention, the membrane is comprised of at least one hydrophobic polymer selected from the group consisting of polysulfones, polyethersulfones, polyamides and polyacrylonitriles and at least one hydrophilic polymer. According to yet another aspect of the present invention, the hydrophilic polymer is selected from the group consisting of polyvinylpyrrolidone (PVP), polyethylene glycol (PEG), polyglycolmonoester, water soluble cellulosic derivates, polysorbate and polyethylene-polypropylene oxide copolymers. The particle content in the polymer spinning solution may vary. According to one aspect, the particle content is from about 0.1 to 12 wt.-% of the spinning solution. According to another aspect, the particle content in the spinning solution is from 1 to 10 wt.-% of the spinning solution. According to yet another aspect of the invention, the particle content is from 1 to 8 wt.-% of the spinning solution.

According to one aspect of the present invention, the doped membranes of the invention are microporous membranes. Microporous membranes are known in the art and can be prepared, for example, according to what is disclosed in EP 1 875 957 A1, incorporated herein by reference. The expression "microporous" as used herein refers to membranes which are characterized by an average pore diameter of the selective separation layer in the membrane in the range of 0.1 to 10 µm, preferably 0.1 to 1.0 µm. In the context of the present invention, the microporous membranes should be designed to allow for the passage of larger components of the fluid to be treated, for example during liver dialysis, especially albumin which has bound thereto toxins which need to be removed in a module according to the invention. Doped microporous hollow fibre membranes can be prepared in a process as described above, comprising the steps of extruding a polymer solution through the outer ring slit of a hollow fibre spinning nozzle, simultaneously extruding a centre fluid through the inner bore of the hollow fibre spinning nozzle, into a precipitation bath, whereby the polymer solution contains 0.1 to 10 wt.-% of hydrophobic and/or ion exchange particles, 10 to 26 wt-% of a hydrophobic polymer, such as polysulfone (PSU), polyethersulfone (PES) or polyarylethersulfone (PAES), 8 to 15 wt-% polyvinylpyrrolidone (PVP), 55 to 75 wt-% of a solvent such as, for example, NMP, and 3 to 9 wt-% water. The centre fluid contains 70 to 90 wt-% of a solvent such as, for example, NMP, and 10 to 30 wt-% water, and the precipitation bath contains 0 to 20 wt-% of a solvent such as, for example, NMP, and 80 to 100 wt-% water.

According to one aspect of the invention, the doped hollow fiber membranes used for preparing the modules of invention are plasma separation membranes. Membranes suitable for plasma separation are known in the art and have been described, for example, in EP 1 875 956 A1 or EP 1 875 957 A1, all incorporated herein by reference. A plasma separation membrane which may be effectively used for preparing a product according to the present invention is an asymmetric plasma separation membrane which exhibits high permeability for the whole spectrum of plasma proteins and lipoproteins, reflected by a high sieving coefficient of >0.90. Further, the doped plasma separation membrane used preferably has an inner diameter in the range of 100 to 500 µm. The doped plasma separation membrane which can advantageously be used for the present invention has a wall thickness in the range of between 20 to 150 µm. Further, the membrane should have a pore diameter on the selective separation layer in the range of 0.1 to 1 µm. Membranes which can be used, in a doped form, in a module according to the invention are also used, for example, in filters known as Plasmylane®.

In yet another aspect of the present invention, the polymer solution used to prepare the membrane of the invention comprises, in addition to the particles, from 12 to 15 wt.-% of polyethersulfone or polysulfone as hydrophobic polymer and from 5 to 10 wt.-% of PVP, wherein said PVP consists of a low and a high molecular PVP component. The total PVP contained in the spinning solution consists of from 22 to 34 wt.-%, preferably of from 25 to 30 wt.-%, of a high molecular weight (>100 kDa) component and from 66 to 78 wt.-%, preferably from 70 to 75 wt.-% of a low molecular weight 100 kDa) component. Examples for high and low molecular weight PVP are, for example, PVP K85/K90 and PVP K30, respectively. The polymer solution used in the process of the present invention preferably further comprises from 66 to 86 wt.-% of solvent and from 1 to 5 wt.-% suitable additives. Suitable additives are, for example, water, glycerol and/or other alcohols. Water is especially preferred and, when used, is present in the spinning solution in an amount of from 1 to 8 wt.-%, preferably from 2 to 5 wt.-%. The solvent used in the process of the present invention preferably is chosen from N-methylpyrrolidone (NMP), dimethyl acetamide (DMAC), dimethyl sulfoxide (DMSO), dimethyl formamide (DMF), butyrolactone and mixtures of said solvents. NMP is especially preferred. The center fluid or bore liquid which is used for preparing the membrane comprises at least one of the above-mentioned solvents and a precipitation medium chosen from water, glycerol and other alcohols. Most preferably, the center fluid consists of 45 to 70 wt.-% precipitation medium and 30 to 55 wt.-% of solvent. Preferably, the center fluid consists of 51 to 57 wt.-% of water and 43 to 49 wt.-% of NMP. Methods for preparing such membranes are disclosed in detail in European Patent Application No. 08008229.

According to another embodiment of the invention, the doped membrane as used in a module according to the invention may be a "protein separation membrane", sometimes also referred to as "plasma purification or "plasma fractionation membrane". Such membrane is characterized by allowing the passage of ≥90% of molecules having a molecular weight of below 100 kD, while molecules having a molecular weight of >1000 kD will pass the membrane wall only to a very limited extend (≤10%). The membrane thus allows to separate plasma in fractions with mainly larger proteins/lipids and smaller proteins, such as, for example, albumin. Membranes of this type are known and also commercially available, for example the "Monet®" filter (Fresenius Medical Care Deutschland GmbH).

According to another embodiment of the invention, the fiber packing density or fiber allocation within the integrated module is in the range of from 15% to 75%. The fibers preferably are homogenously distributed over the length of the cylindrical housing of the filter module, which means that the distance between the single fibers remains essentially the same over the total length of the fibers. In another embodiment of the invention, the fiber allocation is between 20 and 55%. In yet another embodiment of the invention, the fiber allocation is between 45% and 70%. In the context of the present invention, the fiber allocation is calculated from the percentage of the cross section surface allocated by the fibers per utilizable cross section surface in the filter housing. The utilizable cross section surface corresponds to the cross section surface.

The fibers which can be used for producing a module according to the invention can be straight or crimped, wherein crimped fibers are fibers having a certain ondulation which is essentially sinusoidal but may deviate from such sinusoidal ondulation over the length of the fiber, i.e. wavelength and/or amplitude of the crimps of one fiber or of two or more fibers may be different. Ondulated fibers and methods for ondulating fibers are known in the art and have been described, for example, in EP 1 257 333 A1. It is possible to combine straight and crimped fibers in one device. In one embodiment of the invention, all of the fibers in the filter module are ondulated. In another embodiment of the invention, all of the fibers in the filter module are straight fibers.

The uncharged, hydrophobic material which populates the filtrate space of the module according to the invention (see, for example, FIG. 4.), may be chosen from a broad range of materials which are generally known in the art. Possible materials comprise, without limitation, carbonaceous adsorbents, polymer adsorbents and hydrophobic silica or combinations thereof. Examples which can be mentioned are, for example, styrenic polymers like DOWEX™ OPTIPORE™ L493 and V493 or Amberlite® XAD®-2, polydivinylbenzene polymers or styrene-divinylbenzene copolymers (e.g. Amberlite® XAD4 or Amberchrom™ CG161), poly(1-phenylethene-1,2-diyl) (Thermocole), carbon, such as activated carbon or carbon nanotubes, or hydrophobic silica, which is silica that has hydrophobic groups chemically bonded to the surface, or combinations thereof. Hydrophobic silica can be made both from fumed and precipitated silica. Carbon particles which may be used in modules according to the invention can be purchased, for example, as Norit® ROX from Norit. Another material which can be used is known as Ujotit, a copolymer of styrene and divinylbenzene without any functional groups, which is available as Ujotit PA-30, Ujotit PA-40 or Ujotit PA-20. According to one embodiment of the present invention, Ujotit PA-30 is used hydrophobic material in the filtrate space of the module according to the invention. Ujotit PA-30 particles or beads have an average diameter of between 80-200 µm and a specific surface of between 750-850 m²/g.

According to one embodiment of the invention, the integrated module according to the invention comprises a bundle of microporous hollow fiber membranes having incorporated therein 25-40 wt.-% of anion exchange particles which are based on a copolymer of styrene and divinylbenzene and being functionalized with trimethylbenzylammonium groups, wherein the particles have an average diameter of below 20 µm. According to another embodiment, the module further comprises, in the filtrate space of the module, uncharged, hydrophobic particles based on a copolymer of styrene and divinylbenzene without any further functionalization, wherein the particles have an average diameter of between 80-300 µm. According to a further embodiment, the packing density of the hollow fibers in such module is in the range of between 20 and 30%, and the membrane surface area is in the range of from 0.3 to 0.6 m² and the fiber dimensions are in the range of 300-340 µm (inner diameter) and 60-100 µm (wall thickness). According to yet a further embodiment, the module further comprises between 40 and 90 g of the hydrophobic adsorber in the filtrate space.

Figure 3:
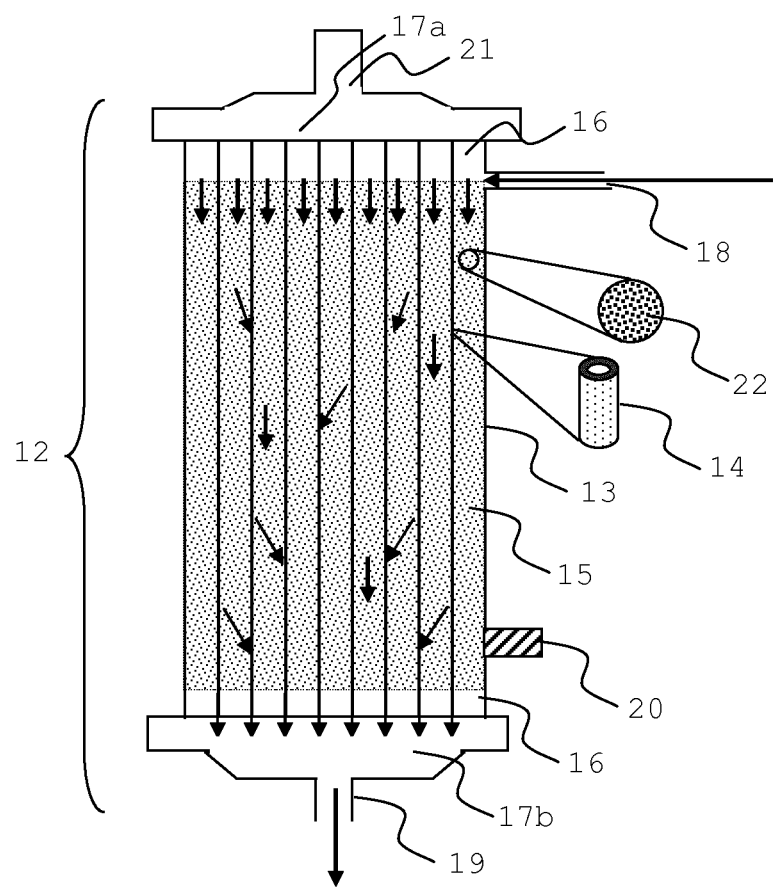
FIG. 3 shows the schematic representation of the integrated device (12) for the removal of liver toxins from a fluid for use in extracorporeal liver support systems according to the invention, wherein the integrated device is a hollow fiber membrane filter module comprising a cylindrical filter housing (13), a bundle of essentially parallel hollow fibers (14) distributed longitudinally within said housing (13), wherein the open ends of the hollow fibers are in fluid communication with a proximal inlet (21), distribution space (17a) and with a collection space (17b), and wherein the ends are embedded in a sealing compound (16) such that the open ends of the hollow fibers (14) extend through the sealing compound (16), a filtrate space (15), which is closed off from the distribution space (17a) and the collection space (17b) and the lumen space of the hollow fiber membranes (14). The filtrate space (15) is also in fluid communication with an inlet means (18) for feeding the fluid comprising the liver toxins into the filtrate space (15) and in fluid communication with the lumen side of the hollow fiber membranes (14), which are in fluid communication with collection space (17b) and outlet means (19) for removing the treated fluid from the housing (13). The integrated device has a second outlet means (20) which may be used for removing treated fluid from the filtrate space (15) alone or in addition to removal of fluid via outlet means (19). The filtrate space (15) is homogenously populated with a particulate material (22) being capable of interacting with components of the fluid, i.e. with the liver toxins which may be present.
Figure 4:
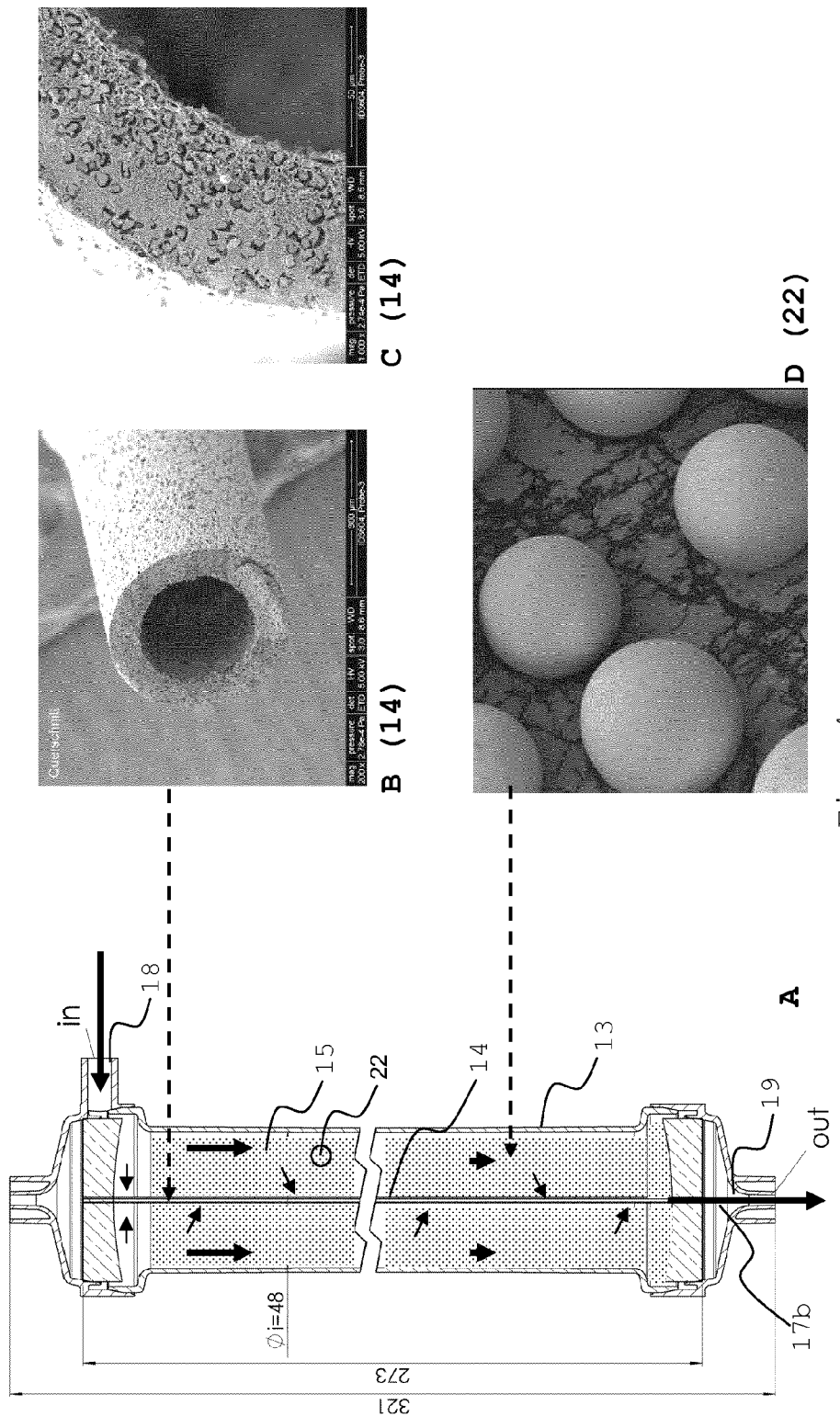
FIG. 4 shows another schematic representation of an integrated device according to the invention (FIG. 4A), including posssible dimensions of the device.

For preparing the module of the invention, the hydrophobic particles can be filled into the filtrate space in their dry state, wherein the filter module is held in an inclined position. The particulate material may also be filled into the filtrate space as a suspension, for example, in water. The dry particulate material or the suspension of the material may be introduced into the filtrate space from top to bottom through inlet port (18). In the alternative, the suspension may be introduced into the filtrate space from bottom to top through outlet port (20), wherein the filter module is held in a vertical position. In the context of the present invention, the expressions "inlet port" and "outlet port" are assigned to certain ports as shown in FIG. 3 and FIG. 4, irrespective of their actual use as an "outlet" or "inlet". For example, an "outlet port" like outlet port (20) may be used to remove fluid from the device and thus serve as an "outlet", but may also be used to introduce fluid into the device, thus serving as an "inlet". However, in order to avoid double assignments, the respective ports have been named either "inlet" or "outlet" ports without restricting the ports to a certain use.

The module according to the invention should be prepared in a way that the filtrate space is homogenously populated with the hydrophobic material. At the same time a high filling ratio is advantageous in order to improve the capacity of the device. Accordingly, a high filling ratio of between 0.6 and 1.0 is desirable, even though lower filling ratios may also serve the purpose. Like that, the modules are designed to provide an optimized permeation of flow so that once the substances present in the fluid to be treated enter the filtrate space of the module they are distributed throughout the active particulate material and will be immobilized or removed with high efficiency. The expression "homogenous" as used herein means that particles it consists of, is evenly distributed over the filtrate space (see, for example, FIG. 11B-11D). This means that the average number of particles per volume, for example $cm^3$, is essentially the same. The expression "essentially the same" used in connection with the average number of particles in a $cm^3$ means that the number of particles in a given volume area of 1 $cm^3$ of the filtrate space may differ from the number of particles in a second volume area of 1 $cm^3$ only by up to 20%. The expression "filling ratio" as used herein, refers to the ratio of the volume in ml of the maximal amount of particulate material, in its dry form or wet form, respectively, which can be accommodated in the filtrate space of a given hollow fiber membrane module ($V_{PM}$) and the utilizable volume in ml of the filtrate space of said module ($V_{FS}$):

$$\text{Filling ratio} = \frac{V_{PM}(\text{ml})}{V_{FS}(\text{ml})}.$$

The volume $V_{PM}(\text{ml})$ of the hydrophobic material which can be accommodated in the filtrate space of a given integrated filter module can be calculated according to the following equation $$V_{PM}(\text{ml}) = \frac{m_{PM}(\text{g})}{\rho(\text{g/ml})},$$

wherein $m_{PM}$ represents the amount of particulate material which could be accommodated in the filtrate space of the module and ($\rho$) refers to the bulk density of the particulate material after compaction ("tapped density"). For a given material $\rho$ can be determined according to DIN ISO 3953.

Figure 5:
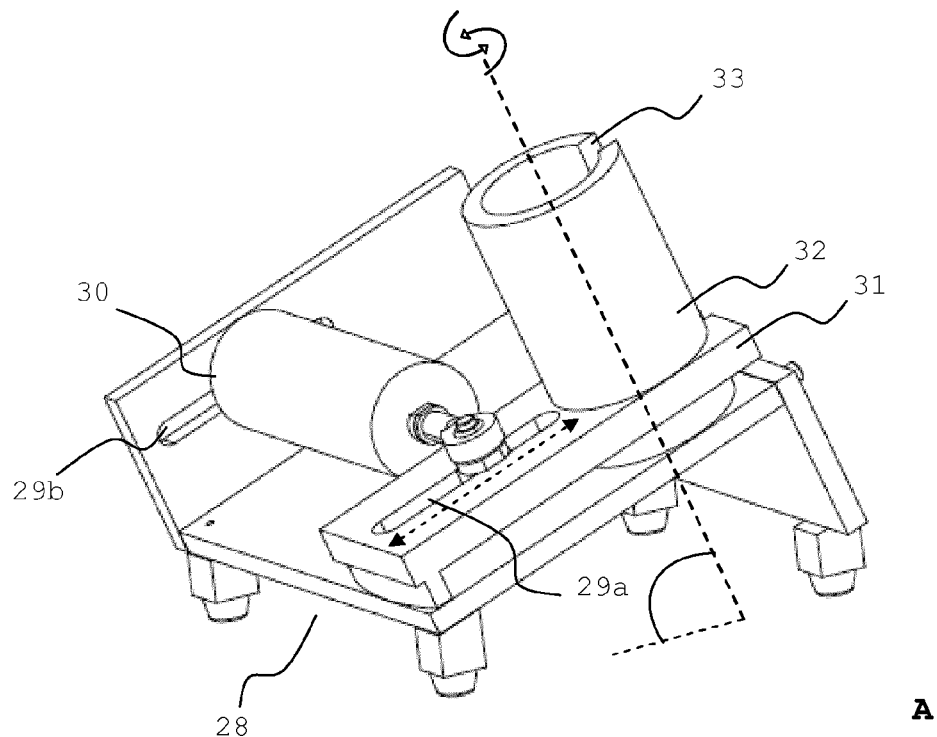
FIG. 5 shows a filling device (28) which may be used to prepare a module according to the invention. The filter module can be positioned in the mounting (32) of the device, which has a slot (33) for accommodating outlet port (20) and optionally also inlet port (18) of the filter module. The mounting (32) is fixed to swiveling unit (31), which is in communication with a pneumatic linear vibrator (30). The vibrator (30) can be moved within slots (29a) and (29b), thereby adjusting the angular displacement of the swiveling unit (31) and the mounting (32). The swiveling unit (31) together with the mounting (32) are designed as a movable element which can be moved back and forth around essentially the longitudinal axis of the module. The filling device (28) may be designed to allow an upright positioning (90°) of the filter module during filling (FIG. 5B) or an inclination of the filter module (FIG. 5A), depending on the filling process (dry or suspension) and the characteristics of the particulate material.
Figure 5:
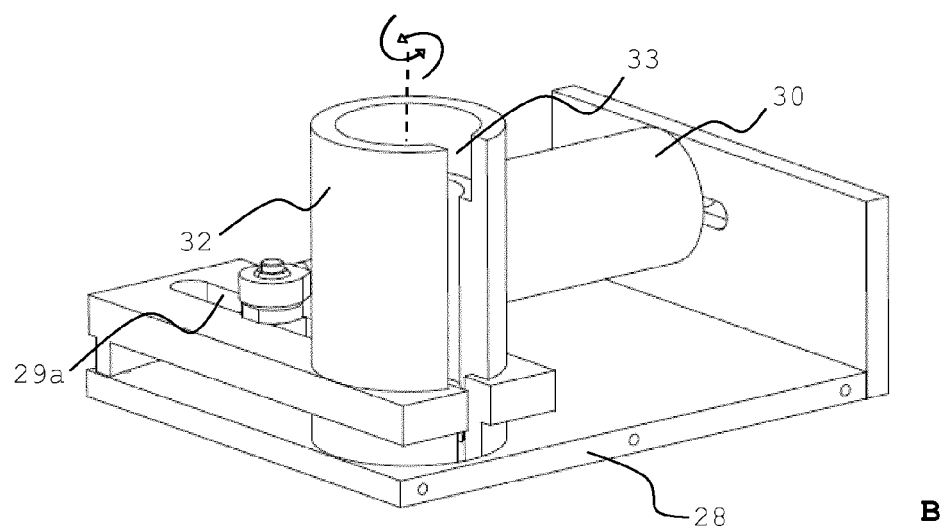

The filling process may be accomplished, for example, with a filling device which is designed to allow positioning the module at a certain angle of inclination, preferably between 45° and 90° C. in regard to its longitudinal axis. Such filling device (FIGS. 5A and 5B) should be designed to optimize the filling process by alternately rotating the hollow fiber filter module clockwise and counter-clockwise around its longitudinal axis in quick succession with a minimum total angular displacement (θ) of about 10°. The rotational movement of the module during filling the filtrate space, optionally in combination with a certain angle of inclination, allows for an improved distribution and deposition of the particulate material between the hollow fibers over the complete utilizable space of the housing. Preferably, the module during the process of filling is additionally exposed to a force which is applied perpendicular to the longitudinal axis of the module with the help of a rapping means. Such pushing or rapping impact on the filter module during filling further improves the homogenous distribution and deposition of the particulate material in the filtrate space. The pushing or rapping force can be achieved, for example, by complementing the filling device as shown in FIG. 5 by a pneumatic interval impactor. It further increases the total amount of particulate material which can be homogenously deposited in the filtrate space of the module. According to one embodiment of the invention, the filling process is accomplished by filling the particulate material into the filtrate space in its wet form. A detailed description of the filling process can be applied for preparing a module according to the invention is described in the European Patent Application entitled "Filter device combining beads and fibers" which was filed by the applicant on the same day as the present application and which is incorporated herein by reference. However, any means or process can be used for introducing the hydrophobic particles into the filtrate space, as long as the particles are distributed within the filtrate space in way that enables an efficient removal of target substances, such as liver toxins, from the fluid to be treated.

Various kinds of housings (13) can be used for preparing a module according to the invention, comprising those known in the art as housings for hemodialyzers, hemodiafilters or plasmafilters. Dialysis filter housings can be produced from a variety of plastic materials by a variety of processes, such as injection molding. For example, polycarbonates and polypropylenes are widely used in a variety of molding and extrusion applications and can also be used for the module disclosed here. For example, it is possible to use a housing which is otherwise used for a standard dialysis filter, such as, for example, the Polyflux®21S housing. However, it is apparent that other housing having different dimensions can be used without deviating from the spirit of the present invention.

According to one aspect of the invention, an integrated device for the removal of albumin bound liver toxins from a fluid for use in extracorporeal liver support systems is provided. Such liver support systems are used for treating conditions of liver failure. The treatment preferably consists in the elimination of protein-bound toxins from the patient's blood wherein the dialysate contains human serum albumin (HSA). According to one aspect of the present invention, the HSA is clean exogenous HSA, which is fed into the dialysate circuit and which remains there. According to another aspect of the present invention, the HSA is endogenous HSA which has been separated from the blood of the patient to be treated and which after cleansing will be returned to the patient.

Preferably, the treatment is directed to removing albumin bound toxins and inflammatory mediators from the blood of patients suffering from liver failure. In the context of the present invention, substances which may induce liver failure or severe damages to the liver or which, in the course of liver failure, have been shown to specifically accumulate and/or negatively affect the patient and which need to be removed by a liver support system and especially by the integrated device of the invention are referred to as "liver toxins". Liver toxins in the sense of the present description thus comprise, for example, bilirubin, bile acids (e.g. chenodeoxycholic acid), certain vasodilators (e.g. aldosterone, norepinephrine, vasopression, plasma renin), metabolites of aromatic amino acids, medium-chain fatty acids and pro- and anti-inflammatory cytokines (e.g. IL6, IL8, IL10, TNFa, sTNFaR1) or drugs that may cause liver damage or failure (e.g. diazepam, acetaminophen, phenyl-butazone). For example, hydrophobic bile acids are cytotoxic at high concentrations and their accumulation within hepatocytes may lead to apoptosis or necrosis. Pro-inflammatory cytokines are believed to mediate hepatic inflammation, apoptosis and necrosis of liver cells, cholestasis, and fibrosis (see, for example, Stauber et al (2010): MARS and Prometheus in Acute-on-Chronic Liver Failure: Toxin Elimination and Outcome. *Trans-plantationsmedizin* 22:333-338). The treatment preferably results in a reduced blood level of such liver toxins. Some liver toxins will not be captured exclusively by the integrated device according to the invention but may be removed, at least in part, also by the hemodialyzer (4) which is part of standard liver support systems. The integrated device according to the invention, however, may increase the portion of such substances which is removed from the patient. Such substances are also covered by the expression "liver toxins" as used in the present invention.

The term "liver failure" in the context of the present invention refers to the inability of the liver to perform its normal synthetic and metabolic function as part of normal physiology. Liver failure thus leads to an insufficient detoxification of albumin, which is followed by an exhaustion of the binding capacity of the albumin and an enrichment of the otherwise albumin-bound toxins, e.g. of unconjugated bilirubin. Treatment is indicated, for example, at a bilirubin concentration of >10 mg/dL. However, there are liver disorders where a liver dialysis treatment is indicated, but which is not characterized by increased bilirubin levels. Disorders which are associated with the expression "liver failure" as used in the present invention include, but are not limited to, hepatorenal syndrome, decompensated chronic liver disease, acute liver failure, graft dysfunction after liver transplantation, liver failure after liver surgery, secondary liver failure, multi organ failure or intractable pruritus in cholestasis.

Figure 2:
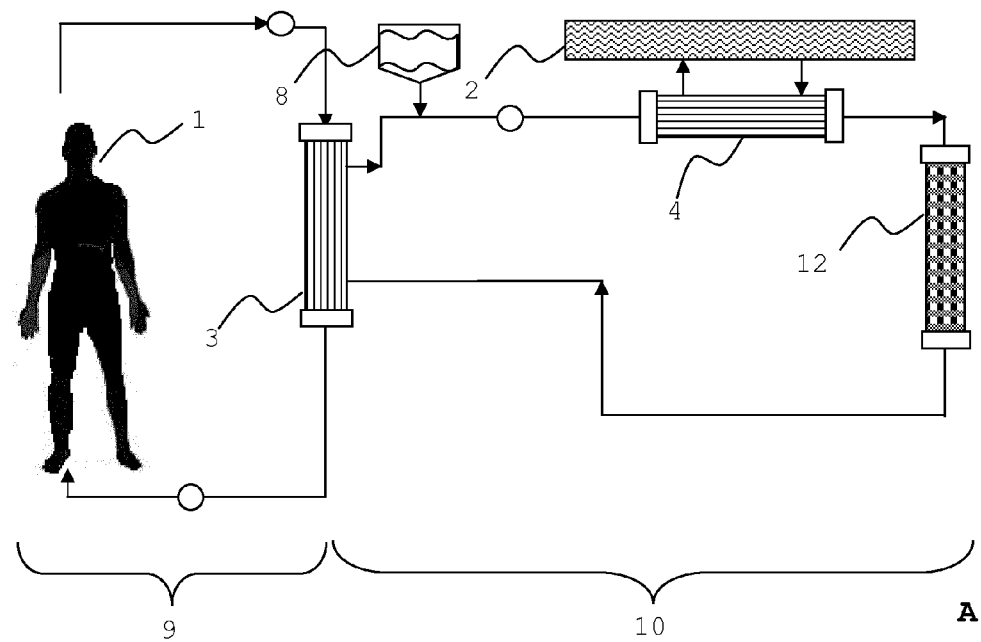
FIG. 2 shows schematic representations of the two liver support setups as described in FIG. 1 after modification according to the present invention. However, the adsorber units (5) and (7) in FIG. 2B and additionally the particle filter (6) in FIG. 2A have been replaced by an integrated device (12) according to the invention.
Figure 2:
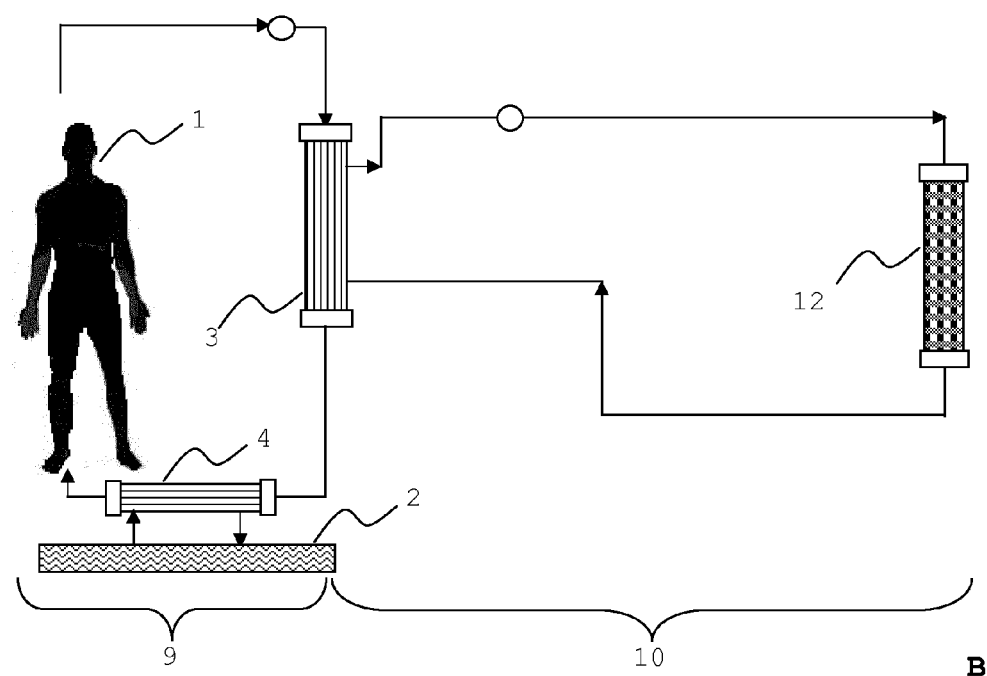

Liver dialysis according to the invention may be carried out (FIG. 2) by passing the patient's (1) blood into a first dialyzer (3). The dialyzer used may contain a standard high-flux membrane such as the MARS® FLUX dialyzer (FIG. 2A), or any other suitable high-flux membrane. It is also possible to use more open-pored membranes in the blood circuit, such as, for example, high cut-off dialysis membranes as described, for example, in EP 10160453.6, which is incorporated herein by reference or a dialyzer such as the AlbuFlow® filter as used in the Prometheus® system (FIG. 2B). The dialysate side of the dialyzer (3) may provide for clean human serum albumin (HSA) that acts as a dialysate (8) (FIG. 2A). In cases where endogenous albumin is allowed to pass the membrane of the first dialyzer (3), the dialysate does not in any case have to provide for such clean exogenous albumin (FIG. 2B). The concentration of the HSA in the dialysate may vary, depending on the approach and the system. In general, it may be in the range of 1% to 25% by weight. Water-soluble and protein bound toxins in the blood are transported through the membrane either bound to endogenous albumin or will pass into the dialysate solution on the other side of the membrane and bind to clean exogenous HSA there, which marks the passage into the albumin circuit (10). The cleansed blood returns to the patient. The albumin in the dialysate or albumin circuit which is carrying the toxins is recycled. In the standard MARS® system (FIG. 1), this is done by passing the fluid first through a standard low-flux dialyzer (4) opposite of a buffered aqueous solution in order to remove water-soluble substances from the albumin. An example for such low-flux dialyzer is the diaFLUX 1.8 dialyzer used in the MARS® system. Afterwards, the albumin passes through an activated carbon adsorber (5). For example, the MARS® system uses vapor-activated carbon, which is used to clean the HSA dialysate in the HSA circuit (e.g. the diaMARS® AC250). The carbon is used for removing low-molecular, non-polar compounds. After passing a filter for removing carbon particles (6), the fluid passes through an anion exchanger (7) that mainly removes anionic molecules, such as bilirubin (e.g. the diaMARS® IE250). The recycled albumin then re-enters the dialyzer (3) and binds again to toxins which can thus be removed from the patient's blood. In the liver treatment and the liver support system according to the invention, the carbon adsorber (5), the carbon particle filter (6) and the anion exchanger (7) can be replaced by the integrated device of the invention (FIG. 2A).

In a system which is operated like the Prometheus® system, the patient's own albumin, in the blood circuit (9), is separated from the blood by a membrane filter (e.g. AlbuFlow®) which allows the passage thereof. In the albumin circuit (10) the albumin then may have to pass two adsorbers (e.g. Prometh® 01 and Prometh® 02), whereby similar to the MARS® system liver toxins are captured and the albumin is set free, which is then returned to the patient. Again, in such system the set of adsorbers can be replaced by one integrated device according to the invention (FIG. 2B).

Flow rates used in liver support systems according to the invention may vary over a certain range and are known to persons with skill in the art. Standard flow rates are, for example, a $Q_B$ (blood flow) of 100-500 ml/min, preferably 150-250 ml/min, a $Q_{Alb}$ (flow in the albumin circuit) of 100-500 ml/min, preferably 150-250 ml/min and a $Q_D$ (dialysate circuit) of 10-1000 ml/min, preferably 50-500 ml/min. Flow rates for replacement fluid may be in the range of, for example, 500-1500 ml/h.

It will be readily apparent to one skilled in the art that various substitutions and modifications may be made to the invention disclosed herein without departing from the scope and spirit of the invention.

The present invention will now be illustrated by way of non-limiting examples of preferred embodiments in order to further facilitate the understanding of the invention.

EXAMPLES

Example 1

Preparation of a Doped Hollow Fiber Membrane 1.1 Grinding of Ion Exchange Resin

Grinding was performed with a LabStar LS1 grinding mill of Netzsch. Dowex 1×2 anion exchanger was grinded in the presence of water and NMP as an organic solvent. Table I summarizes the settings for the grinding procedure.

TABLE I

| | |
|---|---|
| Ion exchange material | Dowex ® 1x2-Cl, 1000 g |
| Solvent | Water/NMP (247.1 g/1300 g) |
| Agitator speed | 3000 l/min |
| Throughput | 74 kg/h |
| Energy input | 3.99 kWh |
| Grinding material | Zirconium oxide |
| Filler Loading | 90% |
| Treatment time | 120 min |
| Particle diameter on cumulative % | d99 = 7.6 μm |

1.2 Preparation of the Spinning Solution

The particles were used for the preparation of a spinning solution for preparing a microporous doped membrane. The polymer composition was chosen to be a combination of hydrophobic polyethersulfone (PES) and a mixture of polyvinylpyrrolidone having high molecular weight (PVP K85) and low molecular weight (PVP K30). The spinning solution further comprised NMP as a solvent and water. The grinding batch of (2.1) was comprised, after grinding, of anion exchange particles (19.88%), NMP (65.21%) and $H_2O$ (14.91%). This suspension was filled into a glass reactor and 1362.97 g NMP were added. The suspension was stirred at $U=600$ $min^{-1}$ until the suspension was homogenous. This was followed by a one hour treatment, under stirring, with an ultrasonic device of Hielscher (UP 400S) for the homogenization and deagglomeration of the suspension. The UP 400S was set to Cycle 1, Amplitude 45% and an energy input of 150W. PVP K85 (180 g) was then added to the suspension and the stirrer was set to 1000 $min^{-1}$. The PVP K85 was dissolved under stirring and ultrasound for one hour. 360 g PVP K30 were then added and also dissolved under stirring and ultrasound. 960 g PES were then added and after 15 minutes the ultrasound device was removed. The stirring velocity was adapted to the apparent viscosity of the suspension. After the PES had completely been solved the average particle size was determined in a particle counter. To this end, 100 μl of the solution were taken and added to 600 ml NMP in a glass bottle. The sample was stirred for about 15 to 20 minutes. The particle counter was set as follows. Channel setting: 16/2-100 μm, sample volume; 5 ml; flow rate: 60 ml/min; number of runs: 9; dilution factor: 1.0; discard first run). The spinning solution ready for spinning was comprised of (wt.-%) grinded Dowex® 1×2 anion exchanger: 8%; NMP: 61%; PVP K85: 3%; PVP K30: 6%; PES: 16%; $H_2O$: 6%.

1.3 Spinning of Doped Hollow Fiber Membranes

For the spinning process, the polymer solution was transferred into a stable stainless steel container. The container was closed and vacuum was applied for degassing the solution. The solution was degassed and then heated to 50° C. and passed through a spinning die (1200×440×220 μm) into the precipitation bath. As center fluid, a mixture of 22% $H_2O$ and 78% NMP was used. The temperature of the die (SD) and of the spinning shaft (SS) can be derived from Table II. The hollow fiber membrane was formed at a spinning speed of between 13.0 and 13.2 m/min (see Table II). The liquid fiber leaving the die was passed into a heated precipitation (water) bath having a temperature of about 65° C. (see Table II). The fiber, at leaving the die, was surrounded by water vapor from the precipitation bath. The distance between the exit of the die and the precipitation bath was 7 to 8 cm (see Table II). The precipitated fiber was guided through several water baths and subjected to online-drying followed by undulation of the fiber. The fibers were transferred into bundles. The resulting hollow fiber membranes had an inner diameter of between 380 and 385 μm and a wall thickness of between 116 and 118 μm (see Table III).

TABLE II

| | Spinning Parameters | | | | | |
|---|---|---|---|---|---|---|
| | Spinning | Distance to Water | Precipitation Bath | | Temperature | |
| Sample | Speed [m/min] | Bath [cm] | T [° C.] | NMP [%] | Spinning Nozzle | Spinning Shaft |
| 2 | 13 | 8[1] | ca. 65 | 0 | 46 | 52-54 |
| 3 | 13.2 | 7[2] | ca. 65 | 0 | 47 | 54 |
| 3a | 13.2 | 7[2] | ca. 64 | 0 | 46 | 53 |

[1]Spinning shaft with 1 cm distance to water surface.
[2]Spinning shaft directly on water surface.

TABLE III

| | Dimensions | |
|---|---|---|
| Sample | Inner diameter μm | Wall thickness μm |
| 2 | 385 | 118 |
| 3 | 383 | 116 |
| 3a | 380 | 115 |

Example 2

Preparation of an Integrated Filter Module
2.1 Preparation of Hand Bundles and Filter Modules Membrane bundles were prepared after the spinning process in order to prepare the fiber bundle for certain performance tests. The first process step is to cut the fiber bundles to a defined length of 23 cm. The next process step consisted of melting the ends of the fibers. An optical control ensures that all fibers were well melted. Then, the ends of the fiber bundle were transferred into a potting cap. The potting cap was fixed mechanically and a potting tube was put over the potting caps. Then the fibers were potted with polyurethane. After the polyurethane had hardened, the potted membrane bundle was cut to a defined length and stored dry before it is used for the different performance tests.

Fiber bundles within a housing were prepared in a similar manner. The manufacturing of the modules comprises the following specific steps. First, the number of fibers required is calculated for the desired effective surface A according to the following equation:

$$A = \pi \times d_i \times l \times n [cm^2],$$

wherein $d_i$ is the inner diameter of fiber [cm], n represents the amount of fibers, and l represents the effective fiber length [cm]. The fiber bundles were cut to a defined length which was adapted to the housing. The fiber bundles were transferred into the housing before the melting process, then put into a vacuum drying oven over night before the potting process.

Microporous hollow fibers prepared according to Example 1 were transferred accordingly into a housing. The fibers had an inner diameter of 320 μm and a wall thickness of 80 μm and contained 30 wt.-% of the Dowex 1×2 anion exchange material (corresponding to 6 g of the material). The module finally contained 20 g of the doped membrane, corresponding to 1400 fibers. The packing density was 24.4%, the membrane area $(A)_{innen}$ amounted to 0.418 m².

2.2 Introduction of Hydrophobic Material into the Filtrate Space

Figure 6:
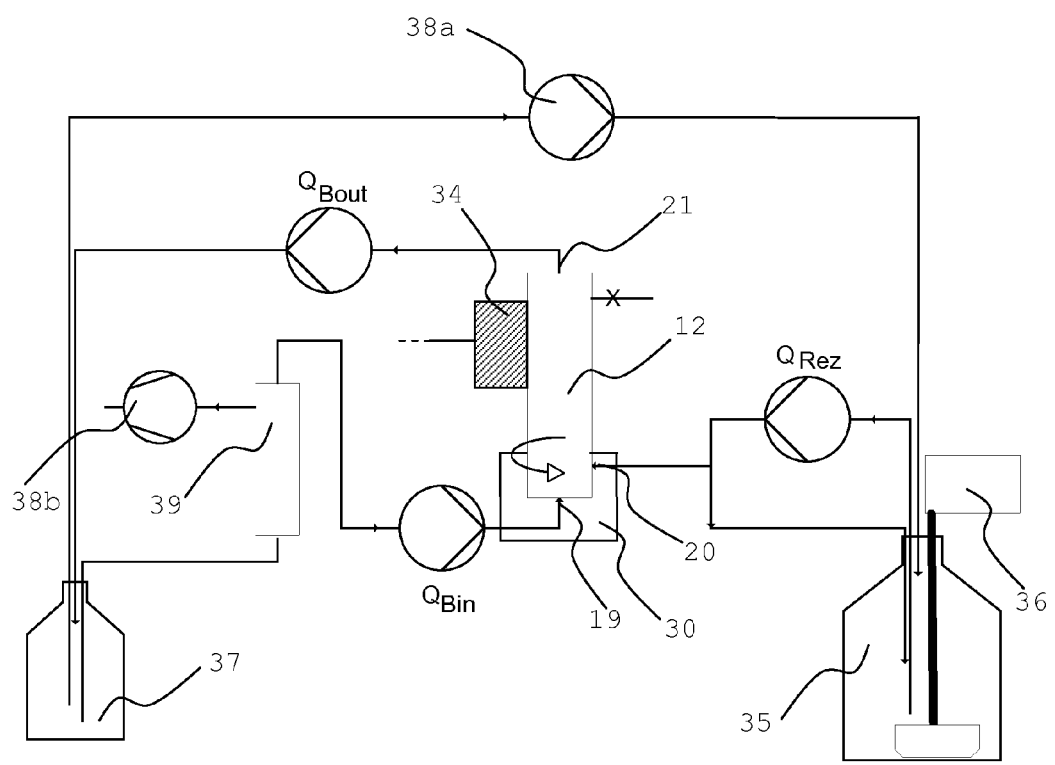
FIG. 6 shows a schematic representation of the process for the suspension filling of the filter module (12), wherein the filter module (12) is held in an upright(90°) position and the suspension of the particulate material is introduced into the filtrate space via outlet port (20). An impactor (34) and vibrator (30) are enabled. The suspension is pumped in ($Q_{Rez}$) from a feed tank (35) which is equipped with a stirrer (36). The solvent leaves the module at inlet port (21), whereas the particulate material remains within the filtrate space, and the solvent is pumped ($Q_{Bout}$) into receiving tank (37). The solvent may be pumped back ($Q_{Bin}$) into the module via outlet port (19) in order to assist in the filling process, wherein a deaeration unit (39), which is in communication with vacuum pump (38b), is used to avoid the introduction of air bubbles. The solvent may also be pumped back via pump (38a) into the feed tank (35). Inlet port (18) is closed.

The module of 2.1 was filled with the hydrophobic adsorber Ujotit PA-30 (Dr. Felgenträger & Co.—Öko-chem. und Pharma GmbH, Dessau-Roßlau, Germany). The material was filled in as a suspension from bottom to top according to FIG. 6. 60 g of the hydrophobic adsorber could be accommodated in the module. The device was then washed with 2 L degassed water followed by 2 L degassed 0.9% NaCl (170 mL/min) to regenerate the anion exchange material within the membrane. The module was then ready to be used.

Example 3

Figure 7:
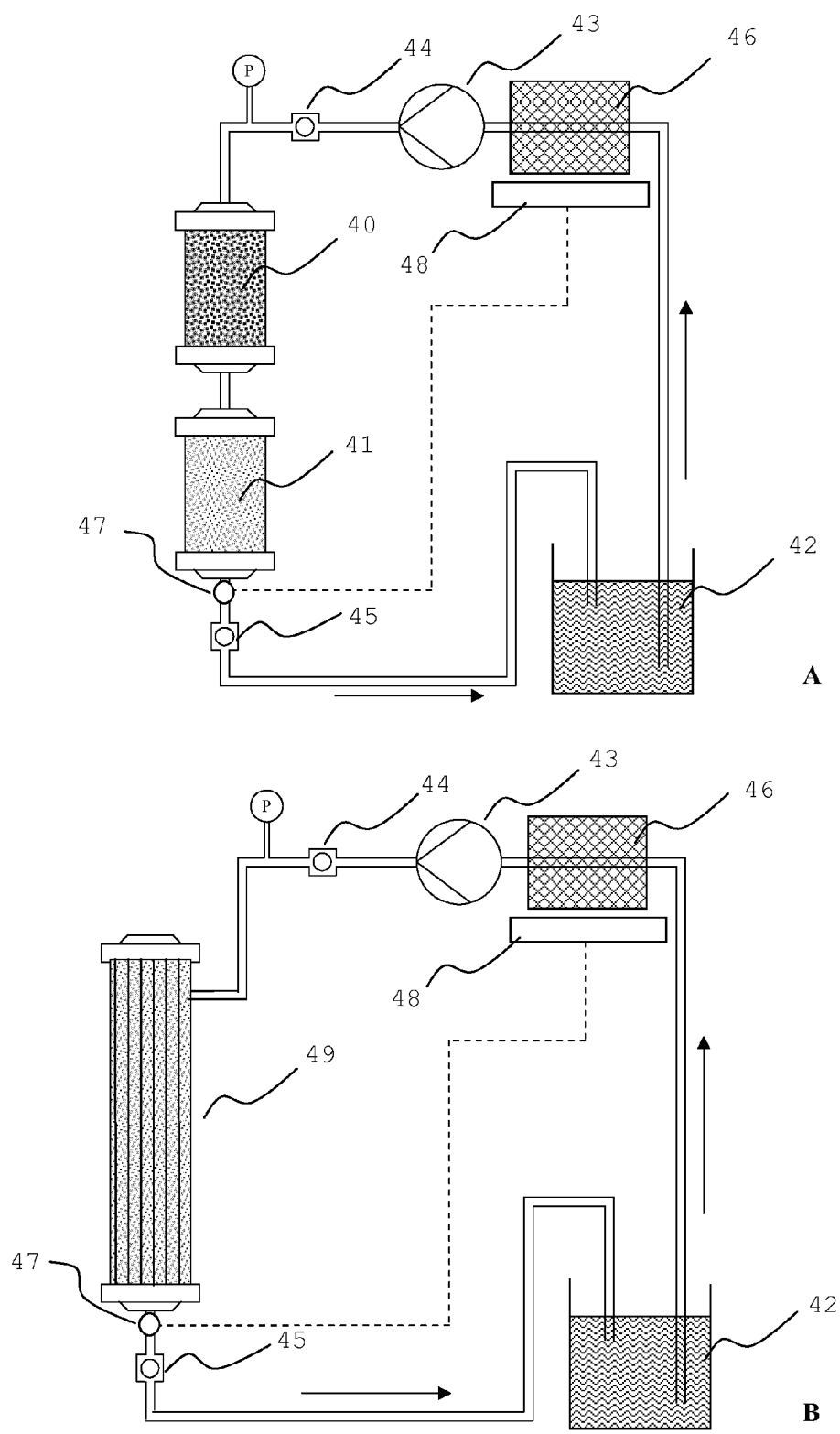
FIG. 7 shows the schematic representations of two test systems for determining the performance of various designs for fluid treatment (see Example 3). The first system (FIG. 7A) comprises the standard adsorber cartridges as they are used, for example, in the MARS® system. The first cartridge (40) contains activated carbon and the second cartridge (41) contains anion exchange material. The second test system (FIG. 7B) comprises the integrated filter module (49) according to the invention. The setup is designed to determine the reduction of certain marker substances by perfusing a solution containing said markers through the cartridges and the integrated filter module, respectively. The marker substances are fed into the system from feed tank (42). The test system further comprises a heat exchanger element (46), supplemented with a magnetic stirrer (48) having connected thereto a contact thermometer (47) which determines the temperature after the respective devices, a pump (43) and specific points (44) and (45) for withdrawing samples for further analysis.

Comparison of the Integrated Filter Module with the Adsorber Units of the MARS® System The integrated filter module according to the invention (see Examples 1 and 2) was compared with the adsorber as used in the MARS® system in a re-circulating test setup (FIG. 7). The first system (FIG. 7A) comprised the standard adsorber cartridges as they are used in the MARS® system. The first cartridge (40) contained activated carbon (Norit® ROX, an acid washed extruded carbon) and the second cartridge (41) contained anion exchange material (Dowex® 1×2). The second test system (FIG. 7B) comprised the integrated filter module (49). The test was based on determining the reduction of certain marker substances by perfusing a solution containing said markers through the cartridges and the integrated filter module, respectively. The marker substances chosen were (a) unconjugated bilirubin from Sigma (UCB, 150 mg dissolved in 15 ml 0.1 M NaOH), (b) chenodeoxycholic acid from Sigma (CDCA, 150 mg dissolved in 15 ml 0.1 M NaOH), (c) diazepam from Sigma (DP, 4.5 mg dissolved in 1 mL ethanol), (d) interleukin-6 from Biosource (IL-6), and (e) human serum albumin solution (HSA, 200 g/L). 15 μl of the IL-6 (100 μg/mL) were dissolved in 185 μL albumin solution (12%). The marker substances were fed into the system from feed tank (42). The test system further comprised a heat exchanger element (46), supplemented with a magnetic stirrer (48) having connected thereto a contact thermometer (47) which determines the temperature after the respective devices, a pump (43) and specific points (44) and (45) for withdrawing samples for further analysis. The pool (42) at the beginning contained 900 g of an HSA infusion solution (200 g/L), 15 mL UCB solution, 15 mL CDCA solution, 1 mL diazepam and 90 μl IL-6 solution (see above). The pool for the integrated filter device (FIG. 7B) further contained 20 mL dialysis solution (taken from 250 mL of the solution containing 235.1 mL degassed water, 7.1 mL acid dialysis concentrate A-Concentrate 242 (NaCl (210.70 g/l), KCl (2.61 g/l), MgCl$_2$×6H$_2$O (1.78 g/l), CaCl$_2$×2H$_2$O (6.43 g/l), CH$_3$COOH (6.31 g/l), water ad 1000 ml) and 8.8 mL bicarbonate dialysis concentrate Type 200 NaHCO$_3$ (35.0 mmol/l in 1.225:35 dilution). The solution finally contained an albumin concentration of 120 g/L. The pool solution was degassed. For filling the system a flow rate of 50 mL/min was used. The flow rate for recirculating the fluid during the test was set to 200 mL/min. The temperature of the system was set to 37° C. (after the devices) and pre-heated for about 30 minutes before re-circulation. The pH in the pool was set to 7.4 with 1 M NaOH. Then recirculation was started. Samples were taken at point (47) after 2, 15, 30, 45 and 60 min and then after 1.5, 2.0, 2.5, 3.0, 3.5, 4.0, 5.0, 6.0 and 12 hours, respectively, and cooled or freezed (for IL-6).

Example 4

Analysis of Marker Substance Reduction

All samples that were obtained in the tests according to Example 4 were analyzed. The UCB samples were photometrically analyzed (440 nm). The samples were diluted (1:5) with 12% HSA solution before the measurement. The CDCA concentrations were determined with the help of a test kit from Trinity Biotech (St. Louis, USA), wherein bile acids are first oxidized to 3-oxo bile acids in the reaction catalyzed by 3a hydroxysteroid dehydrogenase (3αHSD). During this oxidative reaction, an equimolar quantity of nicotinamide adenine dinucleotide (NAD) is reduced to NADH. The NADH is subsequently oxidized to NAD with concomitant reduction of nitro blue tetrazolium salt (NBT) to formazan by the catalytic action of diaphorase. The formazan has an absorbance maximum at 530 nm. The intensity of the colour produced is directly proportional to bile acids concentration in the sample. The diazepam concentrations were determined with the Emit® tox benzodiazepine and barbiturate assays (Dade Behring). The IL-6 concentration was determined with the help of an IL-6 ELISA test kit which is commercially available from different suppliers. The results are shown in FIG. 8 for unconjugated bilirubin, FIG. 9 for chenodeoxycholic acid, FIG. 10 for diazepam and FIG. 11 for interleukin-6.

Figure 8:
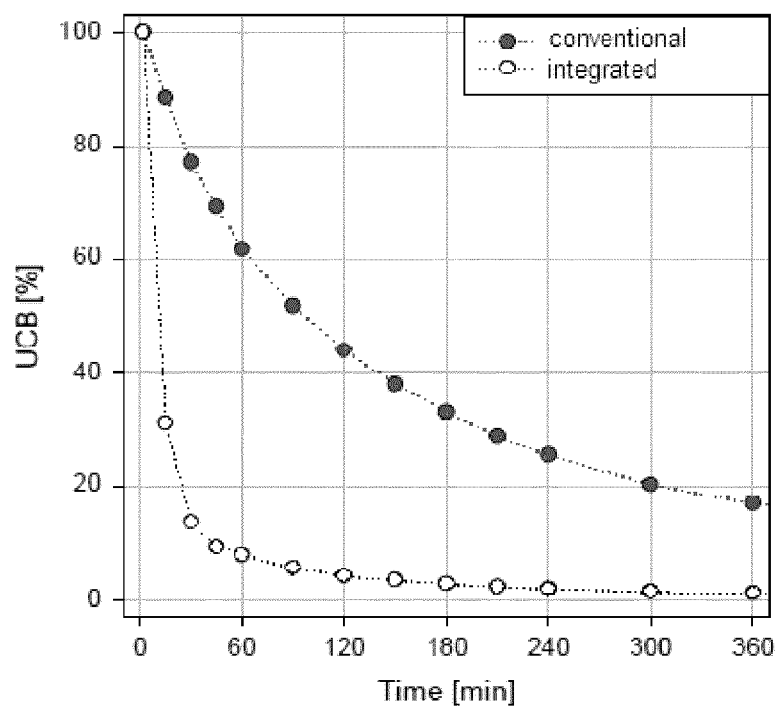
FIG. 8 to FIG. 11 show the results for the reduction of marker substances in the test systems as shown in FIG. 7 (Example 4). Samples that were obtained in the tests according to Example 4 were analyzed. The UCB samples were photometrically analyzed (440 nm). The CDCA and diazepam concentrations were determined as described in Example 4. The IL-6 concentration was determined with the help of an IL-6 ELISA test kit.
Figure 9:
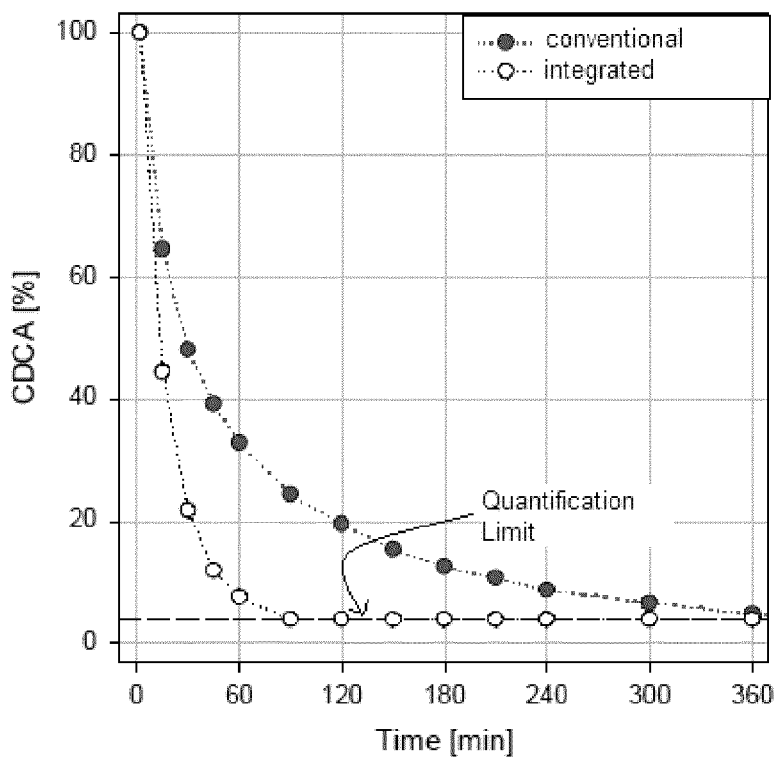
Figure 10:
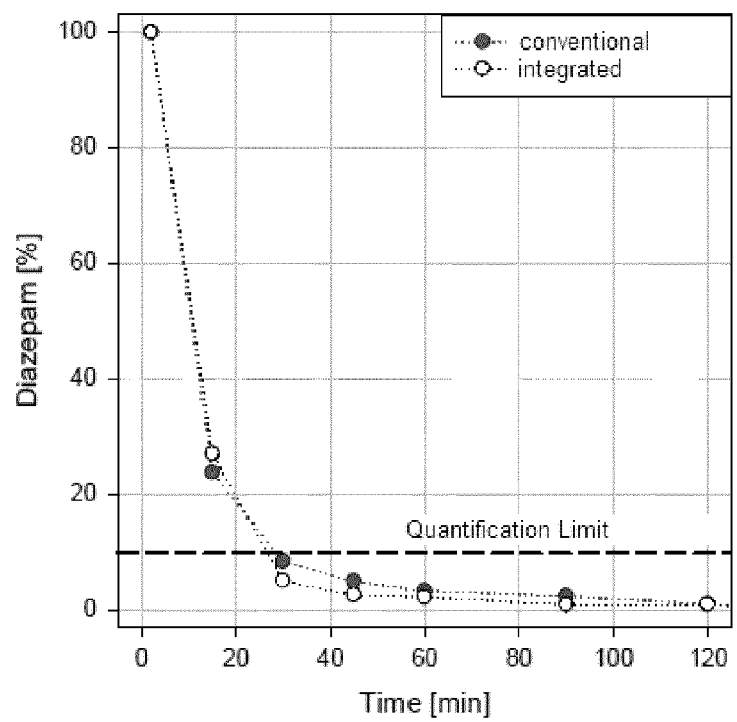
Figure 11:
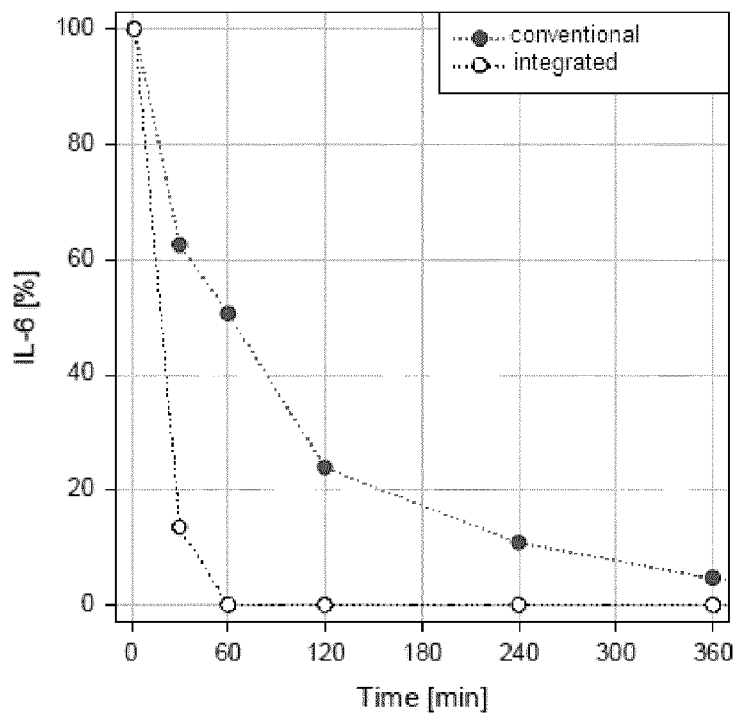
Figure 12:
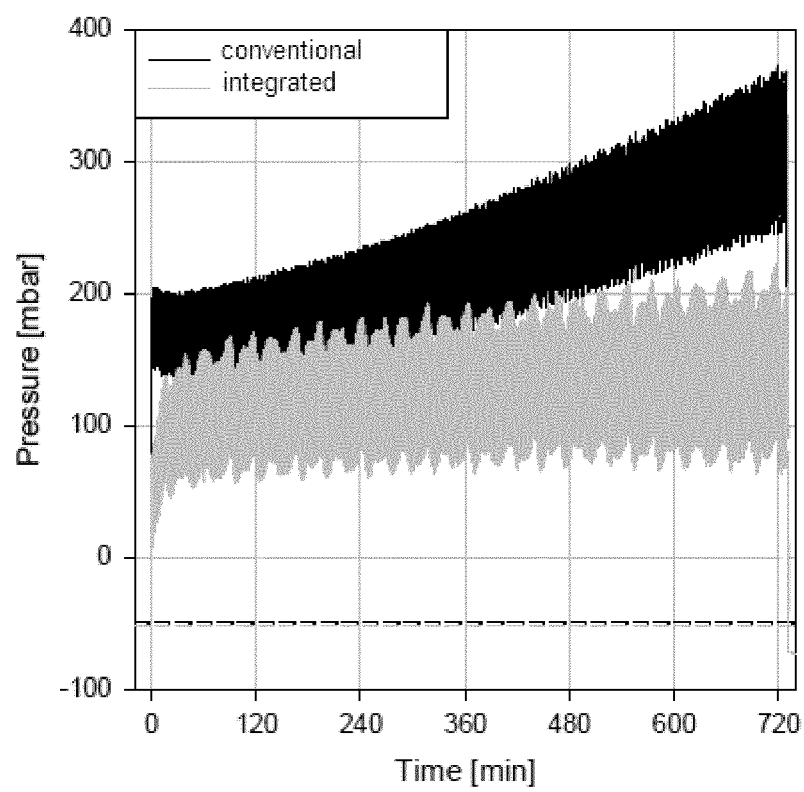
FIG. 12 displays the development of pressure within the two systems which were tested according to Example 3 (see also FIG. 7). Pressure was monitored over 12 hours. A more rapid pressure increase could be seen in the system comprising the conventional cartridges. The pressure also slightly increases over the first 30 minutes at the integrated filter module, but then remains stable for the rest of the test period.

As can be seen in FIG. 8, both systems are able to reduce the concentration of unconjugated bilirubin. However, the integrated filter device of the invention provides for very good adsorption kinetics compared to the conventional combination of adsorber cartridges. After only one hour 10% of the initially available unconjugated bilirubin is left. The adsorber cartridges are not able to arrive at that 10% value even after 6 hours. The adsorption kinetics is also better for the removal of chenodeoxycholic acid from the pool (FIG. 9). In this case, the quantification limit for the bile acid CDCA is reached already after 1.5 hours, whereas the conventional combination of adsorber cartridges needs 6 hours to arrive at that level. For the removal of diazepam no significant difference could be detected between the two approaches. After 30 minutes the quantification limit was already reached (FIG. 10). All values below the quantification limit cannot be regarded as reliable. For IL-6 a difference can be seen between the two approaches. Again, the integrated filter module according to the invention has a significantly better adsorption kinetics and the initial concentration of about 400 pg/ml was reduced very quickly (FIG. 11). The development of pressure within the system was also monitored over 12 hours (FIG. 12). A more rapid pressure increase could be seen in the system comprising the conventional cartridges. The pressure also slightly increases over the first 30 minutes at the integrated filter module, but then remains stable for the rest of the test period.

Example 5

Figure 13:
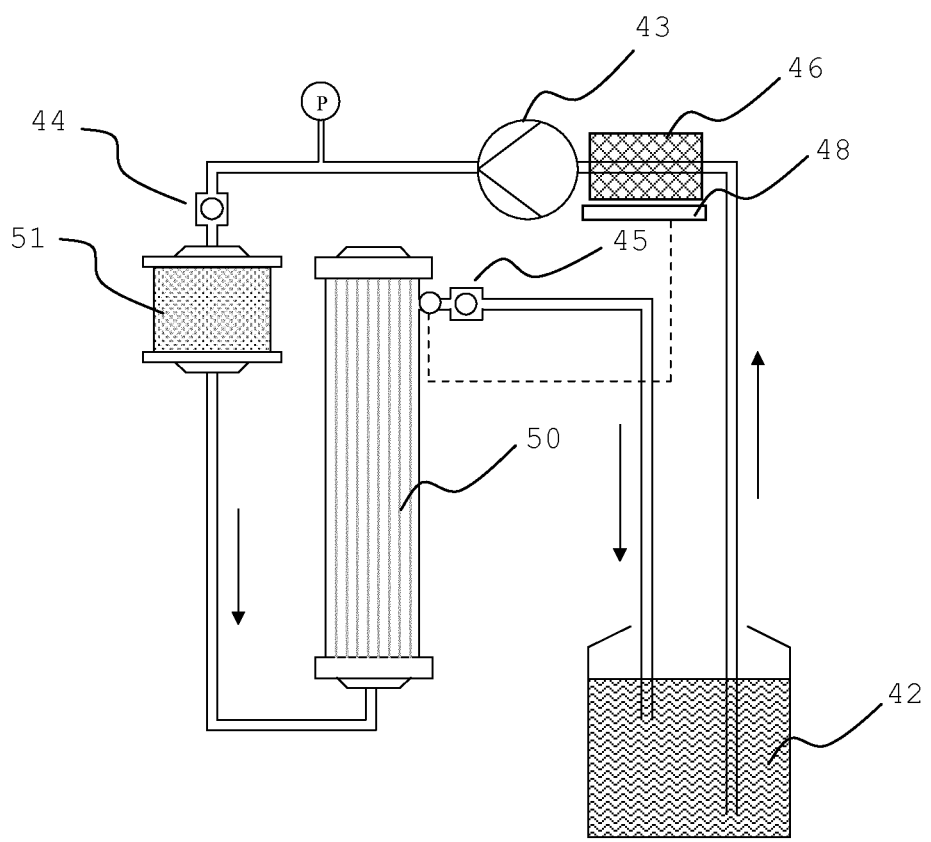
FIG. 13 shows an alternative system setup, wherein the hydrophobic adsorber is provided in a separate cartridge (51) instead of in the filtrate space. The cartridge is installed in line with the filter comprising doped fibers (50).
Figure 14:
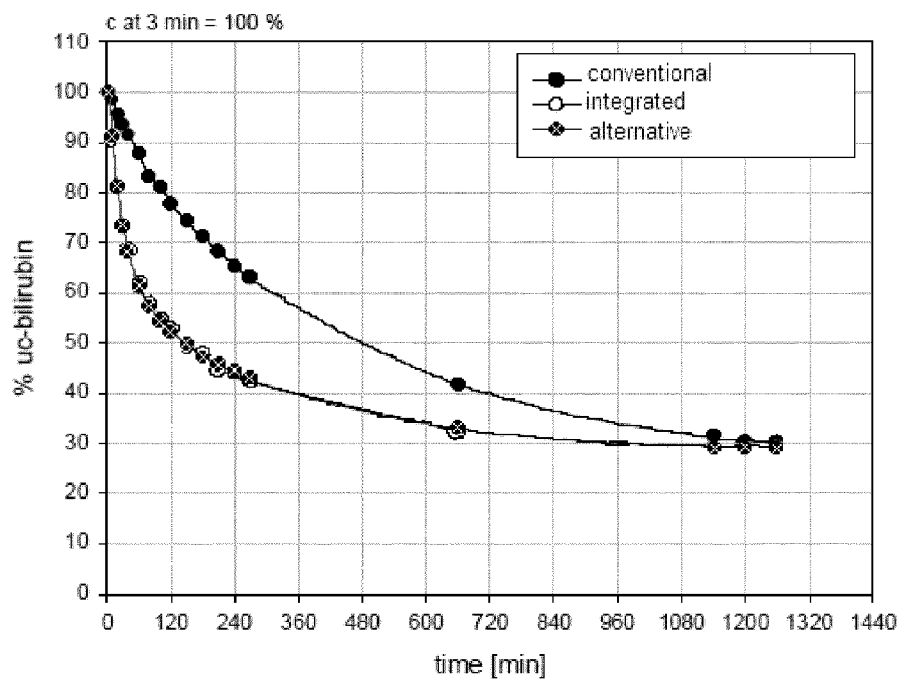
FIG. 14 to FIG. 16 show the results for the reduction of certain marker substances in the test systems according to FIG. 7 in comparison with a setup according to FIG. 13 (see Example 5).
Figure 15:
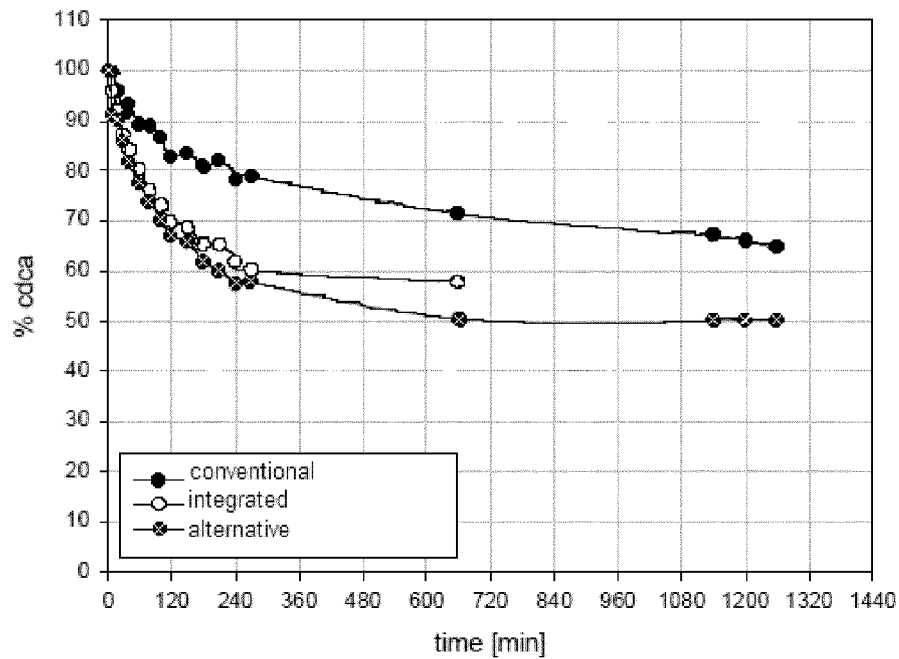
Figure 16:
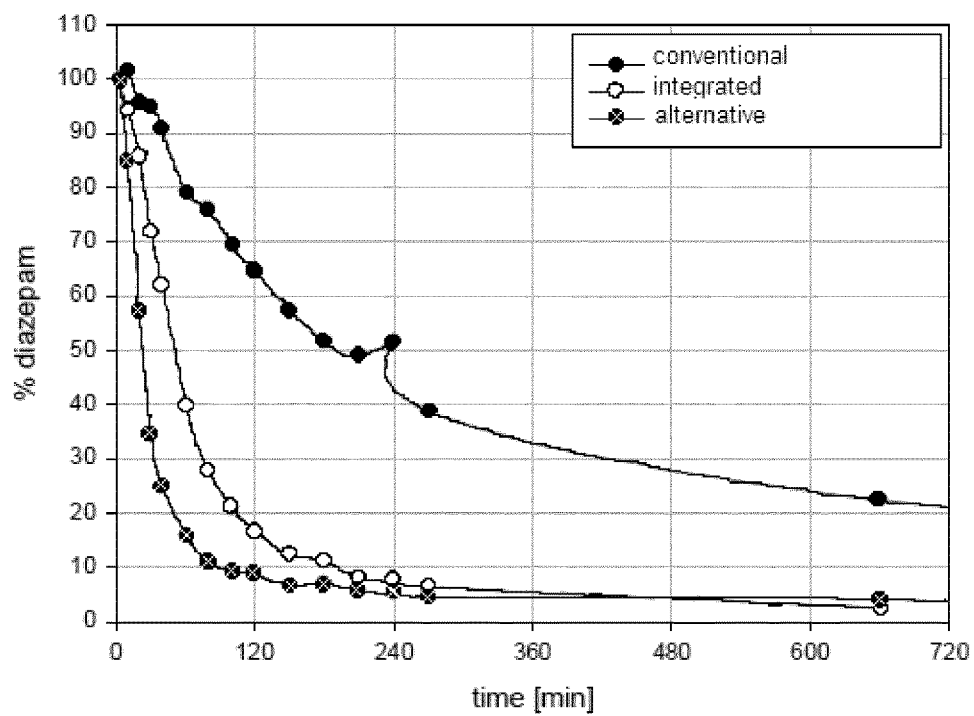

Comparison of the Integrated Filter Module with Alternative Setup According to the Art and the Conventional Cartridge System It is possible also to contemplate the simple combination of a filter comprising doped fibers as described herein and as known in the art and of an adsorber cartridge as described herein and as known in the art. In order to test such conservative approach, a filter was prepared according to the method described in Examples 1 and 2, but without filling hydrophobic adsorber material into the filtrate space. Instead, a cartridge (51) comprising the same hydrophobic adsorber as described before (Ujotit PA-30) was prepared. Care was taken to have the same amount of hydrophobic adsorber in the filtrate space of the cartridge as in an integrated device according to the invention (4.6 g dry weight). Also, the nature and number of fibers within the filter housing (50) and the respective membrane surface area was kept identical (440 fibers with about 550 cm³ surface area; dimensions: 318 µm inner diameter, 77 µm wall thickness, integrated Dowex® 1×2 anion exchanger, ~30%). The filter housings used were smaller than the housings used in Examples 1 to 4 (1:13). In addition, a conventional setup as described before (Ex. 3) comprising two adsorber cartridges was prepared, however again in a smaller version (1:13) to match the other two systems (17.7 ml carbon Norit® ROX, 17.7 mL Dowex® 1×2). The pool volume was 1.5 L, containing 120 g/L (~12%) HSA, 50 mg/L UCB, 25 mg/L CDCA, ~1300 ng/mL diazepam, 400 µg/mL IL-6. The flow rate was set to 50 ml/min. Otherwise, the setup and the experiments were the same as described in Examples 3 and 4. The test setup for an adsorber in a separate cartridge, in line with the filter comprising doped fibers can be reviewed in FIG. 13. The other two setups, in smaller form, were as shown in FIG. 7. FIGS. 14 to 16 show the results for the reduction of selected marker substances, UCB, CDCA and diazepam, respectively.

As can be seen in FIG. 14, the adsorption kinetics is again better for the integrated filter module compared to the conventional cartridge system, especially during the first four hours. The alternative setup with a doped membrane filter and separate cartridge with hydrophobic adsorber performs essentially as good as the integrated system. FIG. 15 shows the results for CDCA reduction. Again, the integrated filter module and the alternative concept with a doped membrane filter and separate cartridge with hydrophobic adsorber perform better than the conventional system with two cartridges. However, the pressure in the alternative design (doped membrane filter and separate cartridge) increased significantly to 0.4 bar after 12 h. Finally, FIG. 16 shows the reduction of diazepam. After about 2 h the quantification limit was already reached with the integrated filter module and the alternative design (doped membrane filter and separate cartridge), whereas here, the conventional cartridge system reached the quantification limit only after 9 h. The development of the pressure in the various system proved to be similar to what was shown before in FIG. 12, wherein the pressure of the alternative system (doped membrane filter and separate cartridge) increased even more than in the conventional cartridge system.

The invention claimed is:

1. An integrated filter module for the treatment of fluids, comprising
   (a) a cylindrical filter housing;
   (b) a bundle of essentially parallel hollow fiber membranes distributed longitudinally within the cylindrical filter housing;
   (c) a filtrate space, which is closed off from a lumen space of the hollow fiber membranes and which is in fluid communication with an inlet means and optionally an outlet means;
   (d) the inlet means for feeding fluid into one of the filtrate space and the lumen space of the hollow fiber membranes;
   (e) the outlet means for removing the fluid from the lumen space of the hollow fiber membranes, and optionally a second outlet means for removing treated fluid from the filtrate space;
   wherein the hollow fiber membranes are prepared from at least one hydrophobic polymer selected from the group consisting of polysulfones, polyethersulfones, polyaryethersulfones, polyamides and polyacrylonitriles and at least one hydrophilic polymer and have incorporated therein at least one of 5-40 wt.-% of ion exchange particles and 5-40 wt.-% of hydrophobic particles, and
   wherein the filtrate space is populated with at least one of hydrophobic particles and ion exchange particles at a filling ratio of between 0.6 and 1.0, wherein the filling ratio is the volume in ml of the maximal amount of particulate material which can be accommodated in the filtrate space of a given hollow fiber membrane module ($V_{PM}$) and the utilizable volume in ml of the filtrate space of said module ($V_{FS}$):

$$\text{Filling ratio} = \frac{V_{PM}(\text{ml})}{V_{FS}(\text{ml})}$$

wherein $V_{PM}$ represents the volume of the particulate material which can be accommodated in the filtrate space of the module, and $V_{FS}$ represents the utilizable filtrate space, and wherein $V_{PM}$ is calculated from $$V_{PM}(\text{ml}) = \frac{m_{PM}(\text{g})}{\rho(\text{g/ml})}$$

wherein $m_{PM}$ represents the amount of particulate material which can be accommodated in the filtrate space of the module and p represents the tapping density of the particulate material according to DIN ISO 3953.

2. A module according to claim 1, wherein the hydrophobic particles of the filtrate space are selected from the group consisting of carbonaceous adsorbents, polymer adsorbents, hydrophobic silica and mixtures thereof.

3. A module according to claim 1 wherein the ion exchange particles of the hollow fiber membranes are one of cation exchange particles and anion exchange particles.

4. A module according to claim 1 wherein the hollow fiber membrane comprises 5-40 wt.-% of ion exchange particles and that the filtrate space is populated with hydrophobic particles.

5. A module according to claim 1 wherein the cylindrical filter housing has an allocation of the hollow fiber membranes between 15% to 70%.

6. A module according to claim 1 wherein the particles in the filtrate space have an average diameter of between 1 µm to 400 µm.

7. A module according to claim 1 wherein the hollow fiber membrane is one of a microporous membrane and a protein separation membrane.

8. A module according to claim 1 wherein the hollow fiber membrane is a plasma separation membrane.

9. A module according to claim 1 wherein the fluid enters the module at inlet means which is in fluid communication with the filtrate space.

10. A module according to claim 1 wherein the fluid enters the module at inlet means which is in fluid communication with a lumen side of the hollow fiber membranes.

11. A module according to claim 1 wherein the fluid is removed from the module through outlet means.

12. A module according to claim 1, wherein the hydrophobic particles of the hollow fiber membranes are selected from the group consisting of carbonaceous adsorbents, polymer adsorbents, hydrophobic silica and mixtures thereof.

13. A module according to claim 1, wherein the hollow fiber membranes have incorporated therein 25-40 wt.-% of ion exchange particles.

14. A module according to claim 1, wherein the filtrate space is homogenously populated with at least one of hydrophobic particles and ion exchange particles.

15. A module according to claim 1, wherein the filtrate space is homogenously populated with hydrophobic particles.

16. A module according to claim 1, wherein the filtrate space is homogenously populated with ion exchange particles.

17. A module according to claim 1, wherein the filtrate space is populated with hydrophobic particles.

18. A module according to claim 1, wherein the filtrate space is populated with ion exchange particles.

* * * * *